United States Patent
Ochiya et al.

(10) Patent No.: US 9,790,492 B2
(45) Date of Patent: Oct. 17, 2017

(54) AGENT FOR TREATING CANCER

(71) Applicants: NATIONAL CANCER CENTER, Tokyo (JP); ASAHI KASEI PHARMA CORPORATION, Tokyo (JP)

(72) Inventors: Takahiro Ochiya, Tokyo (JP); Fumitaka Takeshita, Tokyo (JP)

(73) Assignees: NATIONAL CANCER CENTER, Tokyo (JP); ASAHI KASEI PHARMA CORPORATION, Tokyo (JP)

( * ) Notice: Subject to any disclaimer, the term of this patent is extended or adjusted under 35 U.S.C. 154(b) by 42 days.

(21) Appl. No.: 14/421,337

(22) PCT Filed: Aug. 19, 2013

(86) PCT No.: PCT/JP2013/072064
§ 371 (c)(1),
(2) Date: Feb. 12, 2015

(87) PCT Pub. No.: WO2014/030602
PCT Pub. Date: Feb. 27, 2014

(65) Prior Publication Data
US 2015/0197747 A1    Jul. 16, 2015

(30) Foreign Application Priority Data
Aug. 20, 2012 (JP) ................. 2012-181915

(51) Int. Cl.
| | | |
|---|---|---|
| A61K 31/70 | (2006.01) | |
| C07H 21/02 | (2006.01) | |
| C07H 21/04 | (2006.01) | |
| C12N 15/113 | (2010.01) | |
| A61K 31/7105 | (2006.01) | |
| G01N 33/50 | (2006.01) | |
| C12Q 1/68 | (2006.01) | |
| G01N 33/574 | (2006.01) | |
| C12N 5/00 | (2006.01) | |

(52) U.S. Cl.
CPC ........ *C12N 15/113* (2013.01); *A61K 31/7105* (2013.01); *C12Q 1/6886* (2013.01); *G01N 33/5011* (2013.01); *G01N 33/57407* (2013.01); *C12N 2310/113* (2013.01); *C12N 2310/14* (2013.01); *C12N 2310/141* (2013.01); *C12N 2320/30* (2013.01); *C12Q 2600/106* (2013.01); *C12Q 2600/136* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 7,723,035 B2 | 5/2010 | Croce et al. | |
| 7,888,035 B2 | 2/2011 | Klass et al. | |
| 7,897,356 B2 | 3/2011 | Klass et al. | |
| 8,192,954 B2 | 6/2012 | Klass et al. | |
| 8,211,653 B2 | 7/2012 | Klass et al. | |
| 8,278,059 B2 | 10/2012 | Klass et al. | |
| 8,557,515 B2 | 10/2013 | Croce et al. | |
| 2004/0152112 A1 | 8/2004 | Croce et al. | |
| 2006/0165659 A1 | 7/2006 | Croce et al. | |
| 2007/0287179 A1* | 12/2007 | Tuschl ................. | C12N 15/113 435/455 |
| 2009/0123533 A1 | 5/2009 | Croce et al. | |
| 2010/0004320 A1 | 1/2010 | Elmen et al. | |
| 2010/0151480 A1* | 6/2010 | Taylor ................. | G07F 17/3258 435/6.16 |
| 2010/0173319 A1 | 7/2010 | Croce et al. | |
| 2010/0184046 A1 | 7/2010 | Klass et al. | |
| 2010/0203529 A1 | 8/2010 | Kuslich et al. | |
| 2010/0227325 A1* | 9/2010 | Vilanova .............. | C12Q 1/6883 435/6.1 |
| 2011/0151460 A1 | 6/2011 | Klass et al. | |
| 2011/0159506 A1 | 6/2011 | Klass et al. | |
| 2011/0237450 A1 | 9/2011 | Klass et al. | |

(Continued)

FOREIGN PATENT DOCUMENTS

| | | |
|---|---|---|
| EP | 2 341 145 | 7/2011 |
| JP | 2006-506469 | 2/2006 |

(Continued)

OTHER PUBLICATIONS

Canadian Office Action issued in CA Patent Application No. 2,879,410, dated Mar. 8, 2016.
Extended European Search Report issued in EP Patent Application No. 13830540.4, dated Apr. 15, 2016.
Korean Office Action issued in Korean Patent Appl. No. 10-2015-7002891, dated Jan. 15, 2016, along with an English language translation.
Cummins et al., "The Colorectal MicroRNAome", *Proc. Natl. Acad. Sci.*, vol. 103, No. 10, pp. 3687-3692, 2006.
Landi et al., "Polymorphisms Within Micro-RNA-Binding Sites and Risk of Sporadic Colorectal Cancer", *Carcinogenesis*, vol. 29, No. 3, pp. 579-584, 2008.
Elbashir et al., "Duplexes of 21-nucleotide RNAs Mediate RNA Interference in Cultured Mammalian Cells", *Nature*, vol. 411, pp. 494-498, 2001.
Dyrskjøt et al., "Genomic Profiling of MicroRNAs in Bladder Cancer: miR-129 is Associated with Poor Outcome and Promotes Cell Death In vitro", *Cancer Res.*, vol. 69, No. 11, pp. 4851-4860, 2009.

(Continued)

*Primary Examiner* — Sean McGarry
(74) *Attorney, Agent, or Firm* — Greenblum & Bernstein, P.L.C.

(57) ABSTRACT

[Problem] To provide the following: an agent for treating cancer, particularly an agent for inhibiting cancer cell proliferation or an agent for inhibiting or preventing cancer metastasis; drug that uses the agent; a method for assessing the effect of cancer treatment; a method for estimating the prognosis of cancer treatment; a method for screening for a substance having a cancer proliferation-inhibiting effect; and a method for screening a substance having a cancer metastasis-impeding effect.
[Solution] Provided is a drug containing a nucleic acid formed from a nucleotide sequence having sequence identity of 70% or greater with at least sequence No. 1 or No. 2, wherein the nucleic acid shows protein expression-inhibiting activity.

25 Claims, 7 Drawing Sheets

(56) References Cited

U.S. PATENT DOCUMENTS

| | | |
|---|---|---|
| 2013/0005599 A1 | 1/2013 | Klass et al. |
| 2013/0045882 A1 | 2/2013 | Klass et al. |
| 2013/0178383 A1 | 7/2013 | Spetzler et al. |
| 2013/0184169 A1 | 7/2013 | Klass et al. |
| 2015/0024961 A1 | 1/2015 | Klass et al. |
| 2015/0216892 A1* | 8/2015 | Thibonnier .......... A61K 31/713 424/489 |

FOREIGN PATENT DOCUMENTS

| | | |
|---|---|---|
| JP | 2008-86201 | 4/2008 |
| JP | 2009-532392 | 9/2009 |
| WO | 2007/112754 | 10/2007 |
| WO | 2009/100430 | 8/2009 |
| WO | 2011/057304 | 5/2011 |
| WO | 2012/048236 | 4/2012 |

OTHER PUBLICATIONS

Catto et al., "MicroRNA in Prostate, Bladder, and Kidney Cancer: A Systematic Review", *European Urology*, vol. 59, pp. 671-681, 2011.
"Expression and Clinical Significance of CENP-F Protein in the Bladder Cancer", including an English language Abstract, http://paper.sysu.edu.cn/xwlw/detail.jsp?channelid=65382&record=7426, date-stamped Jun. 13, 2012.
Uchino et al., "Therapeutic Effects of MicroRNA-582-5p and -3p on the Inhibition of Bladder Cancer Progression", *Mol. Ther.*, vol. 21, No. 3, pp. 610-619, 2013.
Chen et al., "MicroRNAs Module Hematopoietic Lineage Differentiation", *Science*, vol. 303, pp. 83-86, 2004.
Veerla et al., "MiRNA Expression in Urothelial Carcinomas: Important Roles of miR-10a, miR-222, miR-125b, miR-7 and miR-452 for Tumor Stage and Metastasis, and Frequent Homozygous Losses of miR-31", *Int. J. Cancer*, vol. 124, pp. 2236-2242, 2009.
Ichimi et al., "Identification of Novel MicroRNA Targets Based on MicroRNA Signatures in Bladder Cancer", Int. J. Cancer, vol. 125, pp. 345-352, 2009.
Huang et al., "MicroRNA-125b Suppresses the Development of Bladder Cancer by Targeting E2F3", *Int. J. Cancer*, vol. 128, No. 8, pp. 1758-1769, 2011.
Seth et al., "RNAi-based Therapeutics Targeting Survivin and PLK1 for Treatment of Bladder Cancer", *Mol. Ther.*, vol. 19, No. 5, pp. 928-935, 2011.
Hurst et al., "High-resolution Analysis of Genomic Copy Number Alternations in Bladder Cancer by Microarray-based Comparative Genomic Hybridization", *Oncogene*, vol. 23, No. 12, pp. 2250-2263, 2004.
Kuokkanen et al., "Genomic Profiling of MicroRNAs and Messenger RNAs Reveals Hormonal Regulation in MicroRNA Expression in Human Endometrium", *Biol. Reprod.*, vol. 82, No. 4 , pp. 791-801, 2010.
Lopez et al., "Differential Effects of miR-34c-3p and miR-34c-5p on SiHa Cells Proliferation Apoptosis, Migration and Invasion.", *Biochem. Biophys. Res. Commun.*, vol. 409, No. 3, pp. 513-519, 2011.
Watanabe et al., "Evaluation of Energy Deposition to the Urinary Bladder Wall Considering Radiosensitive Basal Cells by Beta-ray Emitters", *JAEA—Research 2007-011*, Cover Page, Abstract , Table of Contents, Tables 1-5, Fig. 1, and English-language translation of 2. Method, 2007.
Heffelfinger et al., "Correlation of Global MicroRNA Expression With Basal Cell Carcinoma Subtype", *G3*, vol. 2, pp. 279-286, 2012.
Zheng et al., "MicroRNA-148a Suppresses Tumor Cell Invasion and Metastasis by Downregulating ROCK1 Gastric Cancer", *Clin. Cancer Res.*, vol. 17, No. 24, pp. 7574-7583, 2011.
Kunej et al., "Epigenetic Regulation of MicroRNAs in Cancer: An Integrated Review of Literature", *Mutation Research*, vol. 717, pp. 77-84, 2011.
International Search Report for PCT/JP2013/072064, mailed Nov. 19, 2013, along with an English langugae translation.
WPI Patent Family Member List for JP 2006-506469, WPIX Copyright 2015, Thomson Reuters on STN.
Japanese Office Action issued in JP Patent Application No. 2014-531612, mailed Sep. 15, 2015, along with an English language translation.

\* cited by examiner

[Fig. 1]
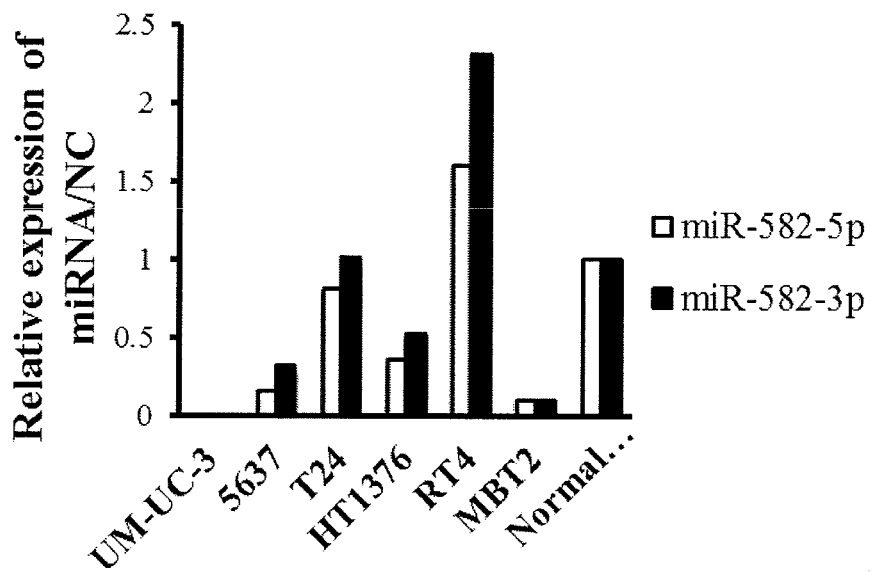
[Fig. 2]
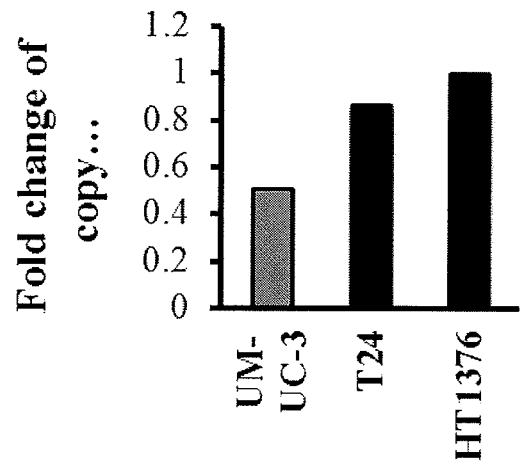

[Fig. 3]
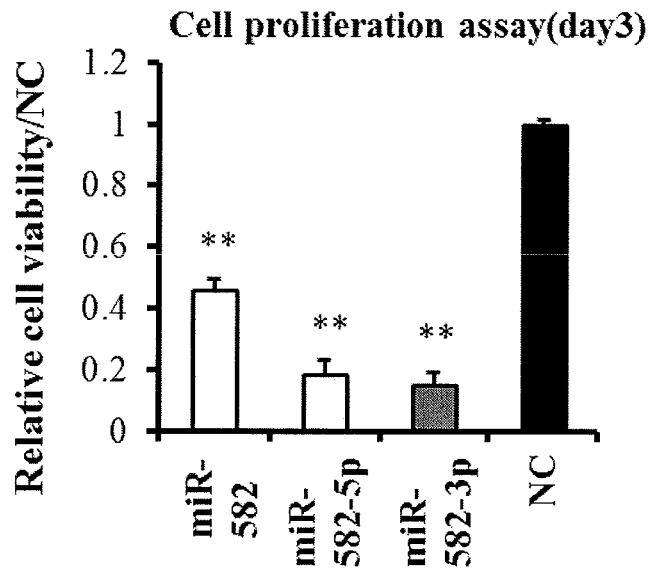
[Fig. 4]
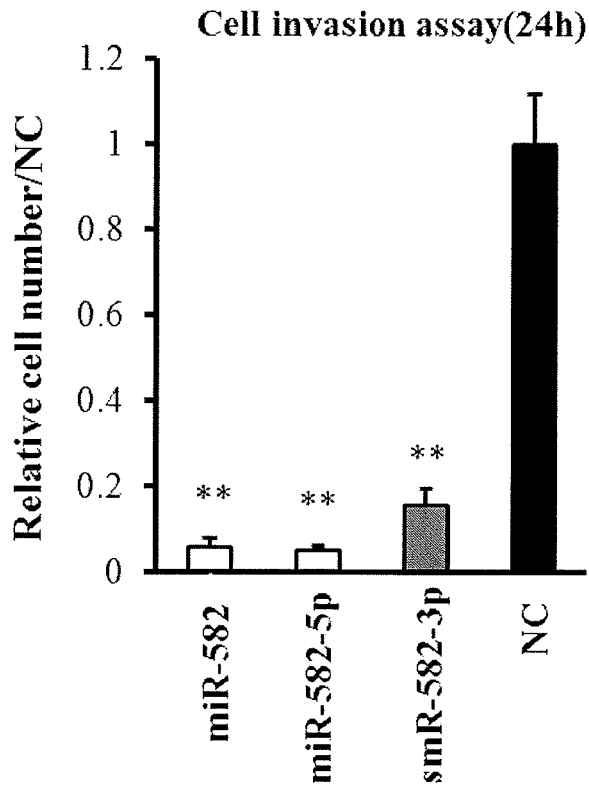

[Fig. 5]
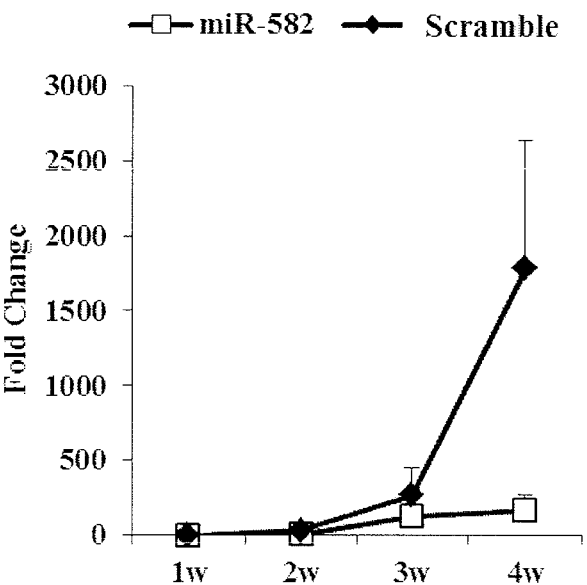
[Fig. 6]
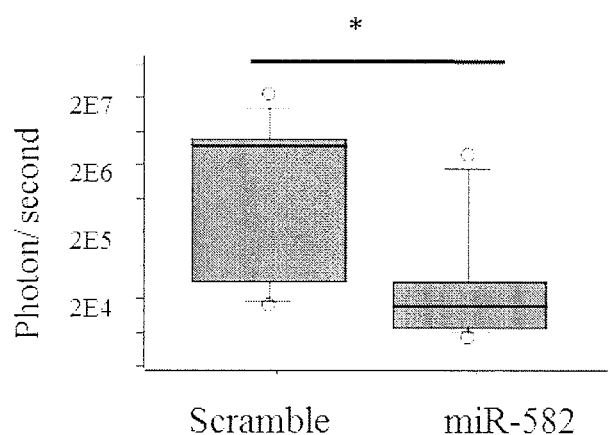

[Fig. 7]
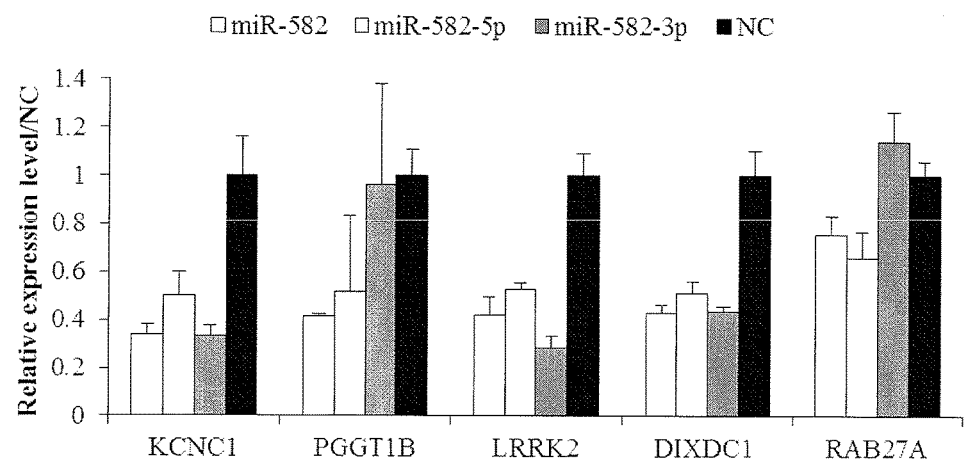
[Fig. 8]
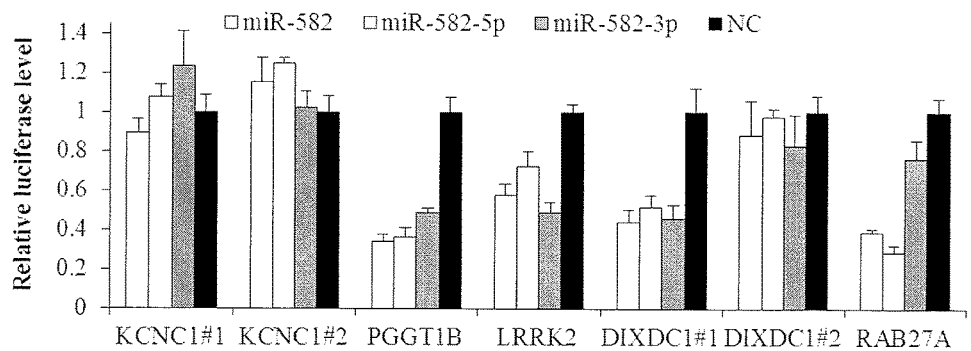

[Fig. 9]
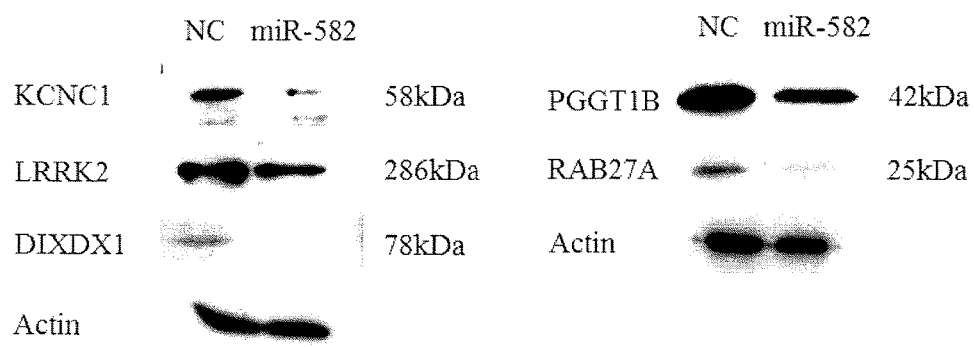
[Fig. 10]
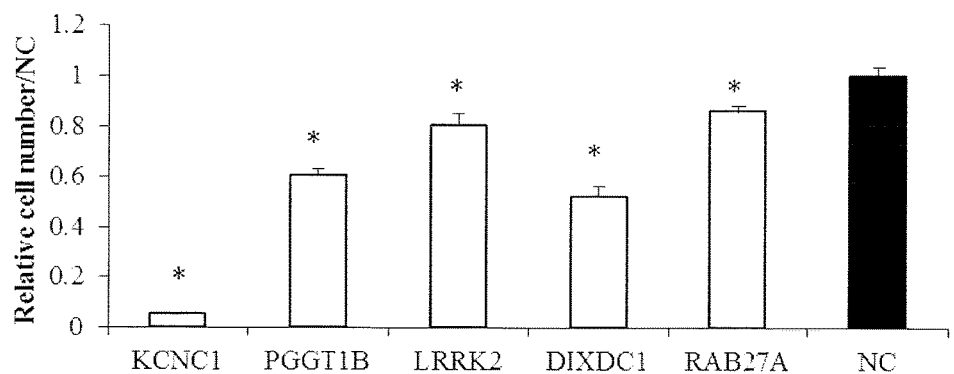

[Fig. 11]
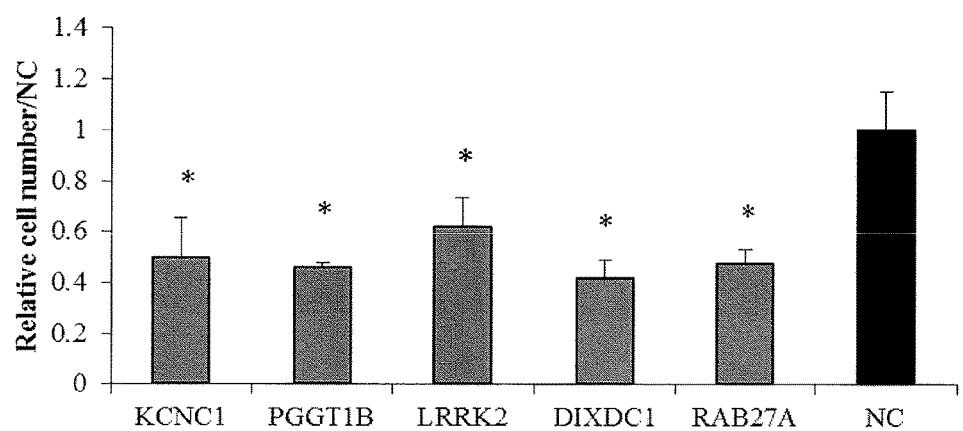

[Fig. 12]
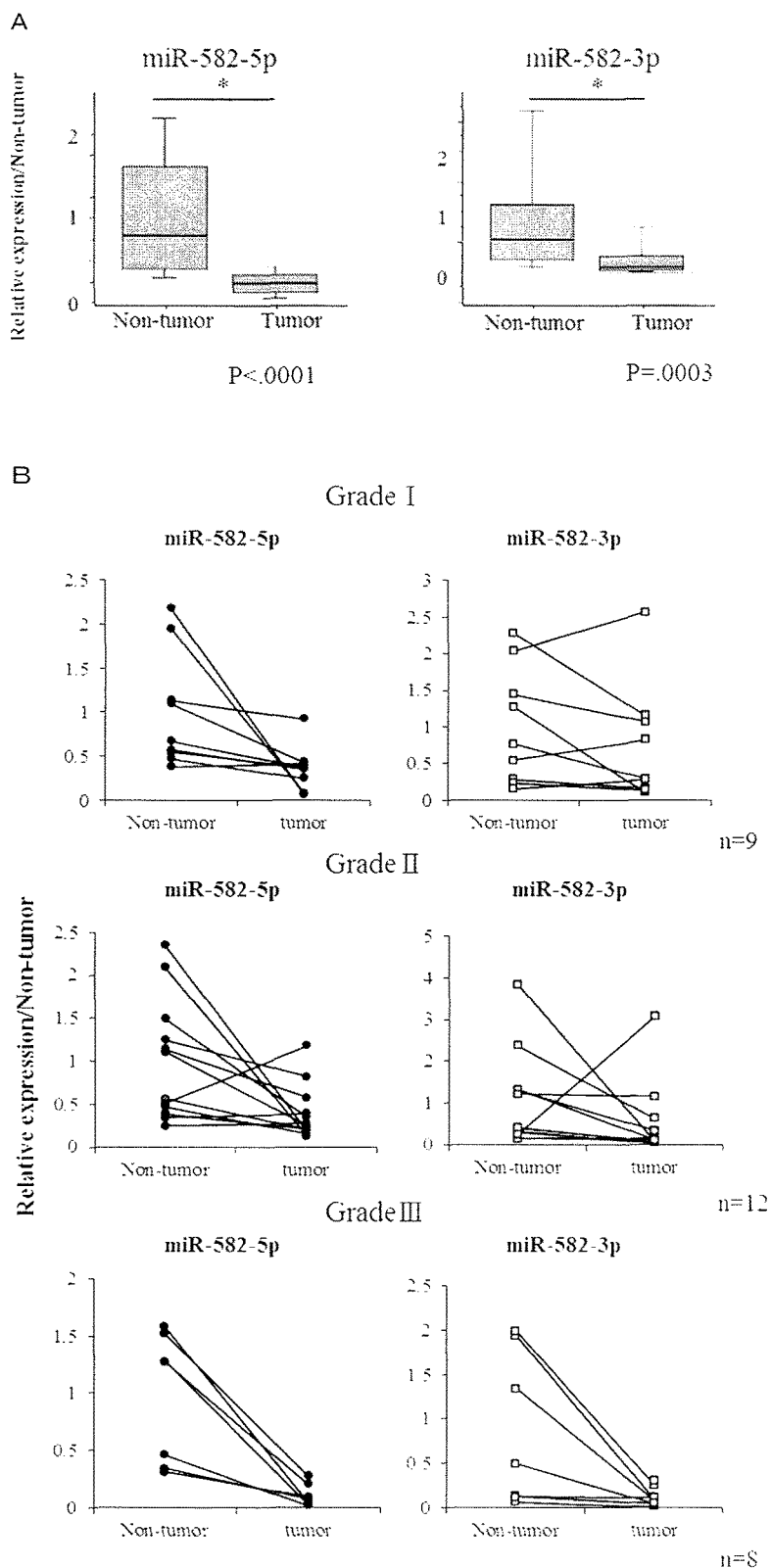

SEQUENCE LISTING

<160> NUMBER OF SEQ ID NOS: 45

<210> SEQ ID NO 1
<211> LENGTH: 23
<212> TYPE: RNA
<213> ORGANISM: Homo sapiens

<400> SEQUENCE: 1
uuacaguugu ucaaccaguu acu                                              23

<210> SEQ ID NO 2
<211> LENGTH: 22
<212> TYPE: RNA
<213> ORGANISM: Homo sapiens

<400> SEQUENCE: 2
uaacugguug aacaacugaa cc                                               22

<210> SEQ ID NO 3
<211> LENGTH: 98
<212> TYPE: RNA
<213> ORGANISM: Homo sapiens

<400> SEQUENCE: 3
aucugugcuc uuugauuaca guuguucaac caguuacuaa ucuaacuaau uguaacuggu      60
ugaacaacug aacccaaagg gugcaaagua gaaacauu                              98

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
ccacaacaag tcaatctgtg c                                                21

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
tattgaaggg ggttctggtg                                                  20

<210> SEQ ID NO 6
<211> LENGTH: 23
<212> TYPE: RNA
<213> ORGANISM: Artificial Sequence
<220> FEATURE:
<223> OTHER INFORMATION: Control sequence

<400> SEQUENCE: 6
uacguacguc gucuaauuaa ucu                                              23

<210> SEQ ID NO 7
<211> LENGTH: 22
<212> TYPE: RNA
<213> ORGANISM: Artificial Sequence
<220> FEATURE:
<223> OTHER INFORMATION: Control sequence

<400> SEQUENCE: 7
auuaauuaga cgacguacga cc    22

<210> SEQ ID NO 8
<211> LENGTH: 30
<212> TYPE: DNA
<213> ORGANISM: Artificial Sequence
<220> FEATURE:
<223> OTHER INFORMATION: Primer

<400> SEQUENCE: 8
aaagaattcg tatgttgctt caagtcattc    30

<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9
aaaggatcca aaggcaccat gtagcttgta    30

<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10
atctgggcgc tcttcgag    18

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
tcgatctccg tcttgttcac    20

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
agcgctattc ttcactcgag ac    22

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
cctgcaggga ataaatccac    20

<210> SEQ ID NO 14
<211> LENGTH: 21
<212> TYPE: DNA

```
<213> ORGANISM: Artificial Sequence
<220> FEATURE:
<223> OTHER INFORMATION: Primer

<400> SEQUENCE: 14
gggctacaac cggaaaaata c                                              21

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
tgatgtccca aacggtcaag                                                20

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
aagaggagga agccatagca c                                              21

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
ccattggcag cactagtttc                                                20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
tacgaagggc aacaaaggtc                                                20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
aatggactcg ctctttgcac                                                20

<210> SEQ ID NO 20
<211> LENGTH: 19
<212> TYPE: DNA
<213> ORGANISM: Artificial Sequence
<220> FEATURE:
<223> OTHER INFORMATION: Primer

<400> SEQUENCE: 20
ggcaccacca tgtaccctg                                                 19
```

```
<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
cacggagtac ttgcgctcag                                              20

<210> SEQ ID NO 22
<211> LENGTH: 30
<212> TYPE: DNA
<213> ORGANISM: Artificial Sequence
<220> FEATURE:
<223> OTHER INFORMATION: Primer

<400> SEQUENCE: 22
gctcgagtaa cccagagttc ttcccattca                                   30

<210> SEQ ID NO 23
<211> LENGTH: 30
<212> TYPE: DNA
<213> ORGANISM: Artificial Sequence
<220> FEATURE:
<223> OTHER INFORMATION: Primer

<400> SEQUENCE: 23
gcggccgcaa agtcagcaca gctggctttt                                   30

<210> SEQ ID NO 24
<211> LENGTH: 30
<212> TYPE: DNA
<213> ORGANISM: Artificial Sequence
<220> FEATURE:
<223> OTHER INFORMATION: Primer

<400> SEQUENCE: 24
gctcgagtaa gctcttttg accaggatgg                                    30

<210> SEQ ID NO 25
<211> LENGTH: 30
<212> TYPE: DNA
<213> ORGANISM: Artificial Sequence
<220> FEATURE:
<223> OTHER INFORMATION: Primer

<400> SEQUENCE: 25
gcggccgcaa tctggtacat accggcagtt                                   30

<210> SEQ ID NO 26
<211> LENGTH: 31
<212> TYPE: DNA
<213> ORGANISM: Artificial Sequence
<220> FEATURE:
<223> OTHER INFORMATION: Primer

<400> SEQUENCE: 26
gctcgagtaa gggggatttg tagcataact g                                 31

<210> SEQ ID NO 27
<211> LENGTH: 30
<212> TYPE: DNA
<213> ORGANISM: Artificial Sequence
<220> FEATURE:
```

<223> OTHER INFORMATION: Primer

<400> SEQUENCE: 27
gcggccgcaa tactttttcc cccaccatca                              30

<210> SEQ ID NO 28
<211> LENGTH: 32
<212> TYPE: DNA
<213> ORGANISM: Artificial Sequence
<220> FEATURE:
<223> OTHER INFORMATION: Primer

<400> SEQUENCE: 28
gctcgagtaa tcacatggaa agggtactca ca                           32

<210> SEQ ID NO 29
<211> LENGTH: 35
<212> TYPE: DNA
<213> ORGANISM: Artificial Sequence
<220> FEATURE:
<223> OTHER INFORMATION: Primer

<400> SEQUENCE: 29
gcggccgcaa caatgaaaga gataacactg gaaca                        35

<210> SEQ ID NO 30
<211> LENGTH: 34
<212> TYPE: DNA
<213> ORGANISM: Artificial Sequence
<220> FEATURE:
<223> OTHER INFORMATION: Primer

<400> SEQUENCE: 30
gctcgagtaa gatgttcata ttgaagcagt caca                         34

<210> SEQ ID NO 31
<211> LENGTH: 30
<212> TYPE: DNA
<213> ORGANISM: Artificial Sequence
<220> FEATURE:
<223> OTHER INFORMATION: Primer

<400> SEQUENCE: 31
gcggccgcaa tgggagtagt ggaaggacag                              30

<210> SEQ ID NO 32
<211> LENGTH: 30
<212> TYPE: DNA
<213> ORGANISM: Artificial Sequence
<220> FEATURE:
<223> OTHER INFORMATION: Primer

<400> SEQUENCE: 32
gctcgagtaa tgaattgttg cttggatgga                              30

<210> SEQ ID NO 33
<211> LENGTH: 33
<212> TYPE: DNA
<213> ORGANISM: Artificial Sequence
<220> FEATURE:
<223> OTHER INFORMATION: Primer

<400> SEQUENCE: 33
gcggccgcaa tgtttgctga gagaaaactg aca                          33

<210> SEQ ID NO 34
<211> LENGTH: 30
<212> TYPE: DNA
<213> ORGANISM: Artificial Sequence
<220> FEATURE:
<223> OTHER INFORMATION: Primer

<400> SEQUENCE: 34
gctcgagtaa ccacaggtaa tgaccaagca                    30

<210> SEQ ID NO 35
<211> LENGTH: 30
<212> TYPE: DNA
<213> ORGANISM: Artificial Sequence
<220> FEATURE:
<223> OTHER INFORMATION: Primer

<400> SEQUENCE: 35
gcggccgcaa tgcaaacccc attttattca                    30

<210> SEQ ID NO 36
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(19)
<223> OTHER INFORMATION: RNA

<400> SEQUENCE: 36
ccaacaaggu agaguucaut t                             21

<210> SEQ ID NO 37
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(19)
<223> OTHER INFORMATION: RNA

<400> SEQUENCE: 37
augaacucua ccuuguuggt t                             21

<210> SEQ ID NO 38
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(19)
<223> OTHER INFORMATION: RNA

<400> SEQUENCE: 38
gagacaagca gguugacaat t                             21

<210> SEQ ID NO 39
<211> LENGTH: 21
<212> TYPE: DNA
<213> ORGANISM: Artificial Sequence
<220> FEATURE:
<223> OTHER INFORMATION: siRNA
<220> FEATURE:

```
<221> NAME/KEY: misc_feature
<222> LOCATION: (1)..(19)
<223> OTHER INFORMATION: RNA

<400> SEQUENCE: 39
uugucaaccu gcuugucuct t                                              21

<210> SEQ ID NO 40
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(19)
<223> OTHER INFORMATION: RNA

<400> SEQUENCE: 40
gcaaaugaac uaagagauat t                                              21

<210> SEQ ID NO 41
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(19)
<223> OTHER INFORMATION: RNA

<400> SEQUENCE: 41
uaucucuuag uucauuugct t                                              21

<210> SEQ ID NO 42
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(19)
<223> OTHER INFORMATION: RNA

<400> SEQUENCE: 42
ggaccagaga guagugaaat t                                              21

<210> SEQ ID NO 43
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(19)
<223> OTHER INFORMATION: RNA

<400> SEQUENCE: 43
uuucacuacu cucuggucct t                                              21

<210> SEQ ID NO 44
<211> LENGTH: 21
<212> TYPE: DNA
<213> ORGANISM: Artificial Sequence
<220> FEATURE:
<223> OTHER INFORMATION: siRNA
```

```
<220> FEATURE:
<221> NAME/KEY: misc_feature
<222> LOCATION: (1)..(19)
<223> OTHER INFORMATION: RNA

<400> SEQUENCE: 44
gaacagaaca gaagggacat t                                              21

<210> SEQ ID NO 45
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(19)
<223> OTHER INFORMATION: RNA

<400> SEQUENCE: 45
ugucccuucu guucuguuct t                                              21
```

AGENT FOR TREATING CANCER

TECHNICAL FIELD

The present invention relates to an agent for treating cancer, particularly to an agent for suppressing cancer cell growth, an agent for suppressing or preventing cancer metastasis, and the like.

BACKGROUND ART

RNA Interference

RNA interference (RNAi) is currently used frequently in life science research, and its utility is widely recognized. RNAi indicates a phenomenon whereby mRNA is degraded sequence-specifically by double-stranded RNA, resulting in suppression of the expression of a gene. In the time since it was reported in 2001 that low-molecular double-stranded RNA of 21 bases can mediate RNAi in mammalian cells (Non-patent Reference 1), siRNA (small interference RNA) has been utilized often as a means of suppressing the expression of a target gene. siRNA is expected to be applied to pharmaceuticals and to be applied to the treatment of various refractory diseases, including cancer.

miRNA miRNA (micro RNA) is an endogenous non-coding RNA of about 20-25 bases encoded on the genome. miRNA is first transcribed as a primary transcript (primary miRNA; referred to hereinafter as "pri-miRNA") of several hundred to several thousand bases in length from a miRNA gene on the genomic DNA, then processed to become pre-miRNA (precursor miRNA) having a hairpin structure of approximately 60-70 bases. It then moves from the nucleus into the cytoplasm and is further processed to become double-stranded mature miRNA of about 20-25 bases. One of the strands of the double-stranded mature miRNA forms a complex with a protein called RISC (RNA-induced silencing complex) and is known to act to inhibit translation of a target gene by acting on the mRNA of the target gene (Non-patent Reference 1). More than 1000 types of miRNA are known in humans, mice, and the like. Each regulates the expression of multiple target genes and is suggested to participate in various life phenomena, such as cell growth, differentiation, and the like. For example, miRNA that participates in the differentiation of hematopoietic cells and neurons has been reported (Non-patent Reference 2). miRNA that participates in the growth of cancer cells has also been reported, and the use of the expression pattern of miRNA in the clinical diagnosis of cancer and methods of treating cancer by suppressing the growth of cancer cells by suppressing the expression of miRNA have been proposed (Patent References 1 and 2). mir582 is known as one of the miRNA (Non-patent Reference 3).

Bladder Cancer

Cancer of the bladder generally arises as a precancerous lesion and can change into invasive cancer. Some can also metastasize and grow. The most common bladder cancer is transitional cell carcinoma of epithelial origin, accounting for 90% of all bladder cancers. Surgical removal is possible for patients with superficial bladder malignancies, but the tendency for recurrence is strong. The five-year survival rate reduces to approximately 50% in the case of bladder malignancies that deeply invade the lower muscle tissue.

In any case, surgery is the main method of treatment of these bladder cancers. The extent of surgery is decided by the disease stage. Early-stage disease can generally be treated by intravesical chemotherapy and transurethral resection. Surgery is often combined with ancillary intravesical infusion of chemotherapeutics or immunotherapeutics to decrease the appearance of cancer at the same site as the bladder wall or other sites and to decrease the severity of recurrence. Definitive (radical) radiotherapy is generally used for bladder cancer patients for whom surgery is not indicated. In the case of superficial or low-malignancy disease, chemotherapy is performed directly within the bladder, the drug is caused to accumulate at the tumor site, and any tumor masses remaining after resection are removed. Systemic chemotherapy is also used for advanced bladder cancer.

Doxorubicin, epirubicin, and such anthracyclines are known to treat bladder cancer. Administration of anthracyclines is believed to reduce the risk of recurrence after surgery, but these compounds have systemic toxicity. This toxicity can be reduced by infusing the drug directly into the bladder, but the drug can enter other organ systems if any type of damage was done to the bladder by surgery. These compounds are also believed to have latent carcinogenicity regardless of the route of administration. It is therefore important to prevent the progression of invasive diseases and to develop safer treatment methods. Bladder cancer also characteristically has a relatively high recurrence rate despite surgical treatment or chemotherapy. The development of treatment methods that lower the recurrence rate is consequently demanded.

PRIOR ART REFERENCES

Patent References

Patent Reference 1: JP Kokai 2008-86201
Patent Reference 2: JP Kokai 2006-506469

Non-Patent References

Non-Patent Reference 1: Elbashir S M et al., Nature, 411: 494-498 (2001)
Non-Patent Reference 2: Science, 303: 83-86 (2004)
Non-Patent Reference 3: Proc. Natl. Acad. Sci., 103: 3687-3692 (2006)

SUMMARY OF THE INVENTION

Problems to be Solved by the Invention

The purpose of the present invention is to provide a more effective method for treating cancer. For example, at least one of an agent for treating cancer, in particular an agent for suppressing cancer cell growth or an agent for suppressing or preventing cancer metastasis, a medicine utilizing these agents, a method for assessing the effect of cancer treatment, a method for predicting the prognosis of cancer treatment, a screening method for substances having a suppressive action on cancer growth, or a screening method for substances having an inhibitory action on cancer metastasis is intended.

Means Used to Solve the Above-Mentioned Problems

"mir582" had not been known up to now to have any relationship whatsoever to cancer cell growth and metastasis. The present inventors discovered for the first time that the expression of "miR582", a type of miRNA, surprisingly is decreased markedly in bladder cancer cells. More importantly, they discovered for the first time that the growth of the cancer cells is suppressed and invasiveness of the cancer cells is suppressed when miR582 is expressed constitutively in bladder cancer cells. In addition, they also discovered that the expression of KCNC1, PGGT1B, LRRK2, DIXDC1, RAB27A, and other such specific RNAs is suppressed in cancer cells transfected with miR582.

Four genes, excluding KCNC1, among the above RNAs the expression of which is suppressed have been suggested to be related to both cancer and cell growth. Specifically, PGGT1B is reported to be involved in the invasion of cancer (Cell Biol. Int., 34: 815-826 (2010)). LRRK2 is reported to phosphorylate Akt and other such proteins involved in cell growth (FEBS Lett., 585: 2165-2170 (2011)). DIXDC1 is also reported to be involved in cell growth (Cancer Sci., 100: 1801-1808 (2009)), and RAB27A is reported to be involved in growth factor secretion (Mol. Cancer. Res., 6: 372-382 (2008)). Without wishing to be bound by theory, suppressing the function of these RNAs may affect the growth and invasiveness of cancer cells.

Furthermore, the present inventors also discovered that the proportion of patients having decreased expression of miR582 increases with the degree of malignancy (grade) of bladder cancer based on analysis using clinical specimens of human bladder cancer.

Therefore, the present invention includes the following:

[1] A medicine for treating cancer characterized by containing at least the following:

(1) a nucleic acid comprising a nucleotide sequence shown by SEQ ID NO: 1 or SEQ ID NO: 2;

(2) a nucleic acid comprising a nucleotide sequence having 70% or higher sequence identity with SEQ ID NO: 1 or SEQ ID NO: 2, the nucleic acid presenting protein expression-suppressing activity, or (3) a single-stranded or double-stranded nucleic acid containing a nucleotide sequence of (1) or (2) above and a sequence complementary to said nucleotide sequence, thereby forming a double-stranded structure in all or part of the strand.

[1-2] The medicine according to [1] above wherein the nucleic acid is a nucleic acid capable of forming a hybrid with at least one RNA selected from the group comprising PGGT1B, LRRK2, DIXDC1, and RAB27A.

[1-3] The medicine according to [1] above wherein the nucleic acid is a nucleic acid capable of suppressing the expression of at least one protein selected from the group comprising KCNC1, PGGT1B, LRRK2, DIXDC1, and RAB27A.

[2] The medicine according to [1] above wherein the nucleic acid is a double-stranded nucleic acid.

Furthermore, when paragraphs that cite [1] such as [1-2] and the like as above are present represented as suffix numbers of [1], that paragraph is also simultaneously cited. This is the same hereinafter.

[3] The medicine according to any one of [1]-[2] above wherein the nucleic acid comprises a nucleotide sequence shown by SEQ ID NO: 1 or a partial sequence thereof.

[3-2] The medicine according to any one of [1]-[2] above wherein the nucleic acid comprises a nucleotide sequence shown by SEQ ID NO: 1.

[4] The medicine according to any one of [1]-[2] above wherein the nucleic acid comprises a nucleotide sequence shown by SEQ ID NO: 2 or a partial sequence thereof.

[4-2] The medicine according to any one of [1]-[2] above wherein the nucleic acid comprises a nucleotide sequence shown by SEQ ID NO: 2.

[5] The medicine according to any one of [1]-[2] above wherein the nucleic acid contains a nucleotide sequence of miR582 and presents protein expression-suppressing activity.

[6] The medicine according to any one of [1]-[2] above wherein the nucleic acid is at least one nucleic acid selected from the group comprising miR582 and precursors thereof.

[6-2] The medicine according to any one of [1]-[2] above wherein the precursor of miR58 is pri-miR582 or pre-miR582.

[7] The medicine according to any one of [1]-[2] above wherein the nucleic acid is miR582.

[8] The medicine according to any one of [1]-[7] above wherein the nucleic acid is a modified nucleic acid.

[9] The medicine according to any one of [1]-[8] above wherein the cancer is a cancer in which the expression of miR582 is decreased.

[10] The medicine according to any one of [1]-[8] above wherein the cancer is bladder cancer.

[11] The medicine according to any one of [1]-[8] above wherein the cancer is bladder cancer of grade 2 or higher.

[12] A medicine for suppressing or preventing metastasis of cancer containing a nucleic acid according to any one of [1]-[8] above.

[13] The medicine according to any one of [1]-[12] above administered transurethrally to a mammal.

[14] A method for predicting the therapeutic effect of The medicine according to any one of [1]-[13] above or a method for assisting in this prediction wherein said method includes a step for measuring the expression level or concentration of a nucleic acid according to SEQ ID NO: 1 or SEQ ID NO: 2 in the cancer.

[14-2] The method according to [14] above including the following steps (1)-(3):

(1) a step for measuring the expression level or concentration of a nucleic acid according to SEQ ID NO: 1 or SEQ ID NO: 2 in normal tissue or normal cells excised from a patient prior to administration of The medicine according to any one of [1]-[13] above and in cancer tissue or cancer cells excised from a patient prior to administration of The medicine according to any one of [1]-[13] above, (2) a step for comparing the expression level or concentration of a nucleic acid according to SEQ ID NO: 1 or SEQ ID NO: 2 between the normal tissue or normal cells and the cancer tissue or cancer cells, and (3) a step for predicting that the medicine according to any one of [1]-[13] above will have a therapeutic effect when the expression level or concentration of a nucleic acid according to SEQ ID NO: 1 or SEQ ID NO: 2 in the cancer tissue or cancer cells is lower than the expression level or concentration of a nucleic acid according to SEQ ID NO: 1 or SEQ ID NO: 2 in the normal tissue or normal cells.

[15] A method for predicting the therapeutic effect of the medicine according to any one of [1]-[13] above or a method for assisting in this prediction including a step for measuring the copy number of the miR582 genome in the cancer.

[15-2] The method according to [15] above including the following steps (1)-(3):

(1) a step for measuring the copy number of the miR582 genome in normal tissue or normal cells excised from a patient prior to administration of The medicine according to any one of [1]-[13] above and in cancer tissue or cancer cells excised from a patient prior to administration of The medicine according to any one of [1]-[13] above, (2) a step for comparing the copy number of the miR582 genome between the normal tissue or normal cells and the cancer tissue or cancer cells, and (3) a step for predicting that the medicine according to any one of [1]-[13] above will have a therapeutic effect when the copy number of the miR582 genome in the cancer tissue or cancer cells is lower than the copy number of the miR582 genome in the normal tissue or normal cells.

[16] A method for assessing the therapeutic effect of The medicine according to any one of [1]-[13] above or a method for assisting in this assessment wherein said method includes a step for measuring the expression level or concentration of a nucleic acid according to SEQ ID NO: 1 or SEQ ID NO: 2 in the cancer.

[16-2] The method according to [16] above including the following steps (1)-(3):

(1) a step for measuring the expression level or concentration of a nucleic acid according to SEQ ID NO: 1 or SEQ ID NO: 2 in cancer tissue or cancer cells excised from a patient prior to administration of The medicine according to any one of [1]-[13] above and in cancer tissue or cancer cells excised from a patient after administration of The medicine according to any one of [1]-[13] above, (2) a step for comparing the expression level or concentration of a nucleic acid according to SEQ ID NO: 1 or SEQ ID NO: 2 between cancer tissue or cancer cells excised from a patient prior to administration of The medicine according to any one of [1]-[13] above and cancer tissue or cancer cells excised from a patient after administration of The medicine according to any one of [1]-[13] above, and (3) a step for assessing that the medicine according to any one of [1]-[13] above has a therapeutic effect when the expression level or concentration of a nucleic acid according to SEQ ID NO: 1 or SEQ ID NO: 2 in the cancer tissue or cancer cells excised from a patient after administration of The medicine according to any one of [1]-[13] above is higher than the expression level or concentration of a nucleic acid according to SEQ ID NO: 1 or SEQ ID NO: 2 in the cancer tissue or cancer cells excised from the patient prior to administration of The medicine according to any one of [1]-[13] above.

[17] A method for assessing the therapeutic effect of the medicine according to any one of [1]-[13] above or a method for assisting in this assessment wherein said method includes a step for measuring the copy number of the miR582 genome in the cancer.

[17-2] The method according to [17] above including the following steps (1)-(3):

(1) a step for measuring the copy number of the miR582 genome in cancer tissue or cancer cells excised from a patient prior to administration of The medicine according to any one of [1]-[13] above and in cancer tissue or cancer cells excised from a patient after administration of The medicine according to any one of [1]-[13] above, (2) a step for comparing the copy number of the miR582 genome between cancer tissue or cancer cells excised from a patient prior to administration of The medicine according to any one of [1]-[13] above and cancer tissue or cancer cells excised from a patient after administration of The medicine according to any one of [1]-[13] above, and (3) a step for assessing that the medicine according to any one of [1]-[13] above has a therapeutic effect when the copy number of the miR582 genome in the cancer tissue or cancer cells excised from a patient after administration of The medicine according to any one of [1]-[13] above is higher than the copy number of the miR582 genome in the cancer tissue or cancer cells excised from the patient prior to administration of The medicine according to any one of [1]-[13] above.

[18] A method for assessing the prognosis of cancer treatment or assisting in this assessment wherein said method includes a step for measuring the expression level or concentration of a nucleic acid according to SEQ ID NO: 1 or SEQ ID NO: 2 in the cancer.

[18-2] The method according to [18] above including the following steps (1)-(3):

(1) a step for measuring the expression level or concentration of a nucleic acid according to SEQ ID NO: 1 or SEQ ID NO: 2 in normal tissue or normal cells excised from a patient and in cancer tissue or cancer cells excised from a patient, (2) a step for comparing the expression level or concentration of a nucleic acid according to SEQ ID NO: 1 or SEQ ID NO: 2 between the normal tissue or normal cells and the cancer tissue or cancer cells, and (3) a step for assessing that the prognosis of cancer treatment is poor when the expression level or concentration of a nucleic acid according to SEQ ID NO: 1 or SEQ ID NO: 2 in the cancer tissue or cancer cells is lower than the expression level or concentration of a nucleic acid according to SEQ ID NO: 1 or SEQ ID NO: 2 in the normal tissue or normal cells.

[19] A method for assessing the prognosis of cancer treatment or assisting in this evaluation wherein said method includes a step for measuring the copy number of the miR582 genome in the cancer.

[19-2] The method according to [19] above including the following steps (1)-(3):

(1) a step for measuring the copy number of the miR582 genome in normal tissue or normal cells excised from a patient and in cancer tissue or cancer cells excised from a patient, (2) a step for comparing the copy number of the miR582 genome between the normal tissue or normal cells and the cancer tissue or cancer cells, and (3) a step for assessing that the prognosis of cancer treatment is poor when the copy number of the miR582 genome in the cancer tissue or cancer cells is lower than the copy number of the miR582 genome in the normal tissue or normal cells.

[20] The method according to any one of [14]-[19] above wherein the cancer is bladder cancer.

[21] A composition for assessing the effect of The medicine according to any one of [1]-[13] above including a nucleic acid probe capable of specifically detecting a nucleic acid according to SEQ ID NO: 1 or SEQ ID NO: 2.

[22] A method for screening substances capable of suppressing the growth of cancer including the following steps (1)-(3):

(1) a step for bringing a test substance and cells that permit measurement of the expression of a nucleic acid according to SEQ ID NO: 1 or SEQ ID NO: 2 into contact, (2) a step for measuring the expression level of a nucleic acid according to SEQ ID NO: 1 or SEQ ID NO: 2 in cells that have been brought into contact with the test substance and comparing the expression level with the expression level of a nucleic acid according to SEQ ID NO: 1 or SEQ ID NO: 2 in control cells that have not been brought into contact with the test substance, and (3) a step for selecting a test substance that upregulates the expression level of a nucleic acid according to SEQ ID NO: 1 or SEQ ID NO: 2 as a substance capable of inhibiting the growth of cancer based on the results of comparison in (2) above.

[23] A method for screening substances capable of inhibiting the metastasis of cancer or the invasive capacity of cancer cells including the following steps (1)-(3):

(1) a step for bringing a test substance and cells that permit measurement of the expression of a nucleic acid according to SEQ ID NO: 1 or SEQ ID NO: 2 into contact, (2) a step for measuring the expression level of a nucleic acid according to SEQ ID NO: 1 or SEQ ID NO: 2 in cells that have been brought into contact with the test substance and comparing the expression level with the expression level of a nucleic acid according to SEQ ID NO: 1 or SEQ ID NO: 2 in control cells that have not been brought into contact with the test substance, and (3) a step for selecting a test substance that upregulates the expression level of a nucleic acid according to SEQ ID NO: 1 or SEQ ID NO: 2 as a substance capable of inhibiting the metastasis of cancer or the invasive capacity of cancer based on the results of comparison in (2) above.

[24] An agent for suppressing the expression of at least one protein selected from the group comprising KCNC1, PGGT1B, LRRK2, DIXDC1, and RAB27A characterized by including at least the following:

(1) a nucleic acid comprising a nucleotide sequence shown by SEQ ID NO: 1 or SEQ ID NO: 2, (2) a nucleic acid comprising a nucleotide sequence having 70% or higher sequence identity with SEQ ID NO: 1 or SEQ ID NO: 2 wherein the nucleic acid presents expression-suppressing activity on at least one protein selected from the group comprising KCNC1, PGGT1B, LRRK2, DIXDC1, and RAB27A, or (3) single-stranded or double-stranded nucleic acid containing a nucleotide sequence of (1) or (2) above and a sequence complementary to that sequence, thereby forming a double-stranded structure in all or part of the strand.

Advantages of the Invention

The present invention makes it possible to provide at least one of an agent for treating cancer, in particular an agent for treating bladder cancer, an agent for suppressing or preventing metastasis of cancer, and a medicine utilizing the above agent. The present invention also makes it possible to provide at least one of a method for assessing the therapeutic effect on cancer, a method for predicting the prognosis of cancer treatment, a method for screening substances having a suppressive action on the growth of cancer, and a method for screening substances having an inhibitory action on the metastasis of cancer.

BRIEF DESCRIPTION OF THE DRAWINGS

FIG. 1 is a graph showing the expression level of miR582 in various bladder cancer cells. In the graph "Normal" shows normal cells, and the numbers on the vertical axis represent the ratio in relation to Normal.

FIG. 2 is a graph showing the copy number of the chromosomal region of miR582 in various bladder cancer cells. The numbers on the vertical axis represent the ratio in relation to HT1376 cells.

FIG. 3 is a graph showing suppression of the growth of human bladder cancer cell lines by miR582. In the graph, "NC" shows the negative control, and the numbers on the vertical axis represent the ratio in relation to NC.

FIG. 4 is a graph showing suppression of the invasive capacity of human bladder cancer cell lines by miR582. In the figure, "NC" shows the negative control, and the numbers on the vertical axis represent the ratio in relation to NC.

FIG. 5 is a graph showing the therapeutic effect of miR582 administration in a mouse bladder cancer model. In the figure, Scramble is a negative control.

FIG. 6 is a graph showing the cancer metastasis-suppressing effect of miR582 administration in a mouse bladder cancer model. In the figure, Scramble is a negative control.

FIG. 7 is a graph showing the suppression of the gene expression of KCNC1, PGGT1B, LRRK2, DIXDC1, and RAB27A by miR582. In the figure, "NC" shows the negative control, and the numbers on the vertical axis represent the ratio in relation to NC.

FIG. 8 is a graph showing that PGGT1B, LRRK2, DIXDC1, and RAB27A are direct target molecules of miR582 and KCNC1 is an indirect target molecule. In the graph, "NC" shows the negative control, and the numbers on the vertical axis represent the ratio in relation to NC.

FIG. 9 is a graph showing the suppression of the protein expression of KCNC1, PGGT1B, LRRK2, DIXDC1, and RAB27A by miR582. In the graph, "NC" shows the negative control.

FIG. 10 is a graph showing the suppression of human bladder cancer cell line growth by transfecting siRNA for the above target genes of miR582. In the graph, "NC" shows the negative control, and the numbers on the vertical axis represent the ratio in relation to NC.

FIG. 11 is a graph showing the suppression of human bladder cancer cell line invasion by transfecting siRNA for the above target genes of miR582. In the graph, "NC" shows the negative control, and the numbers on the vertical axis represent the ratio in relation to NC.

FIG. 12 is a graph showing the expression level of miR582 in human clinical specimens of bladder cancer.

BEST MODE FOR CARRYING OUT THE INVENTION

The present invention is explained concretely below based on preferred embodiments (abbreviated hereinafter as "this embodiment"), but the scope of the present invention is not limited to the specific aspects explained below. The nucleotide sequences in this specification and the sequence listings are described using the RNA sequence for the sake of convenience, but this does not mean that the nucleic acid specified by that sequence or a corresponding sequence number shows only RNA, but should be understood to also show the nucleotide sequence of DNA and chimeric nucleic acid by reading U (uracil) as T (thymine) as appropriate.

As shown in the examples below, the present invention intends to utilize "miR582" and functional analogs thereof as an active ingredient of cancer therapeutics based on the discovery and proof that "miR582" (1) has a function to suppress the growth of cancer cells, in particular bladder cancer cells, (2) has a function to suppress the invasion or metastasis of cancer cells, in particular bladder cancer cells, and (3) has decreased expression in the cancer tissues of human bladder cancer patients.

1. Active Ingredient a. Nucleic Acid Shown by SEQ ID NO: 1 or 2 and Functional Analogs First, nucleic acids comprising a nucleotide sequence represented by SEQ ID NO: 1 (sometimes called "miR582-5p" hereinafter) or SEQ ID NO: 2 (sometimes called "miR582-3p" hereinafter) can be given as examples as this embodiment relating to an active ingredient. These nucleic acids are the most typical active ingredients of the present invention. Functional analogs of these nucleic acids can also be used as active ingredients of the present invention.

Namely, in this specification, the term "functional analogs" indicates nucleic acids that do not completely match the native sequence in any one or a combination of the nucleotide sequence, higher structure, or chemical structure, but can demonstrate at least one of the desired bioactivities of the present invention explained below. For example, functional analogs in this embodiment include nucleic acids comprising a nucleotide sequence having 70% or higher, preferably 80% or higher, more preferably 90% or higher, even more preferably 95% or higher, especially 97% or higher, and ideally 99% or higher sequence identity with SEQ ID NO: 1 or 2.

Furthermore, "identity" of a nucleotide sequence means the percentage (%) of the same nucleotide residues to all overlapping nucleotide residues in the optimal alignment where two nucleotide sequences are aligned using a mathematical algorithm known in the art (preferably, the algorithm considers introduction of gaps into one or both of the sequences for the best alignment). Nucleotide sequence identity can be calculated by, for example, aligning the two nucleotide sequences using the homology calculation algorithm NCBI BLAST-2 (National Center for Biotechnology Information Basic Local Alignment Search Tool) under the following conditions (gap open=5 penalties; gap extension=2 penalties; x_dropoff=50; expectation value=10; filtering=ON).

Other suitable functional analogs of this embodiment can consist of nucleotide sequences having one or multiple nucleotides deleted, replaced, inserted, or added to a nucleotide sequence represented by SEQ ID NO: 1 or SEQ ID NO: 2. Examples of such nucleotide sequences include:

(1) nucleotide sequences having 1-6 (preferably 1-3, more preferably 1 or 2) nucleotides deleted in a nucleotide sequence represented by SEQ ID NO: 1 or SEQ ID NO: 2, (2) nucleotide sequences having 1-6 (preferably 1-3, more preferably 1 or 2) nucleotides added in a nucleotide sequence represented by SEQ ID NO: 1 or SEQ ID NO: 2, (3) nucleotide sequences having 1-6 (preferably 1-3, more preferably 1 or 2) nucleotides inserted in a nucleotide sequence represented by SEQ ID NO: 1 or SEQ ID NO: 2, (4) nucleotide sequences having 1-6 (preferably 1-3, more preferably 1 or 2) nucleotides replaced by another nucleotide in a nucleotide sequence represented by SEQ ID NO: 1 or SEQ ID NO: 2, or (5) nucleotide sequences having a combination of the variations of (1)-(4) above (in this case, the sum of mutated nucleotides is 1-6 (preferably 1-3, more preferably 1 or 2)).

b. Partial Sequences

Functional analogs of this embodiment preferably consist of a "partial sequence" of SEQ ID NO: 1 or SEQ ID NO: 2. "Partial sequence" as relates to this embodiment means a nucleic acid containing a minimum nucleotide sequence necessary for miRNA to recognize a target gene. The existence of this minimum nucleotide sequence as a seed sequence is well known (Proc. Natl. Acad. Sci., 104: 19291-6 (2007)). Namely, the nucleotide sequence of numbers 2-8 from the 5' end called the seed sequence is extremely important in miRNA, and many of the mRNAs that serve as a target for this miRNA have sequences complementary to this seed sequence in their 3' untranslated region. In this way, the miRNA recognizes a specific mRNA having a sequence complementary to its seed sequence and suppresses its function. Since the seed sequence is constructed of a short sequence of seven bases, one miRNA can target multiple mRNAs having sequences complementary to the seed sequence and manifest the inherent miRNA activity. 5'-UGACAUU-3' can be given as an example of the seed sequence of SEQ ID NO: 1. 5'-GGUCAAU-3' can be given as an example of the seed sequence of SEQ ID NO: 2. Therefore, an active ingredient in this embodiment may consist of the above seed sequence of SEQ ID NO: 1 or 2 or may have 15 or more bases, more preferably 17 or more bases, even more preferably 19 or more bases, and ideally 20 bases, including this seed sequence.

c. Nucleic Acid Length and Structure

On the other hand, the length of the nucleic acids and functional analogs in this embodiment (these nucleic acids and functional analogs are sometimes collectively termed "nucleic acids of the present invention" or "nucleic acids of this embodiment" and the like hereinafter) has no upper limit as long as they present at least one of the desired activities of the present invention discussed below. However, in consideration of the ease of synthesis, problems of antigenicity, and the like, the length of the nucleic acids of this embodiment is, for example, 200 or fewer bases, preferably 130 or fewer bases, more preferably 50 or fewer bases, and ideally 30 or fewer bases, as the upper limit. The lower limit is, for example, 7 or more bases, typically 15 or more bases, preferably 17 or more bases. Furthermore, in this specification, the length of the nucleic acid is to be calculated as the length of a single strand even when the nucleic acid forms a partially double-stranded structure by taking on a hairpin loop structure.

Namely, the nucleic acids of this embodiment are not limited to single-stranded nucleic acids and may be in double-stranded form. Double-stranded embodiments include double-stranded RNA, double-stranded chimeric nucleic acids, RNA/DNA hybrids, RNA/chimeric nucleic acid hybrids, chimeric nucleic acid/chimeric nucleic acid hybrids, and chimeric nucleic acid/DNA hybrids. Furthermore, the term chimeric nucleic acid means that RNA and DNA are contained in a single nucleic acid in a single-stranded or double-stranded nucleic acid. A hybrid nucleic acid means a nucleic acid in which one strand is RNA or chimeric nucleic acid and the other strand is DNA or chimeric nucleic acid in a double strand. Generally speaking, the nucleic acid of this embodiment is preferably a single-stranded RNA, single-stranded chimeric nucleic acid, double-stranded RNA, double-stranded chimeric nucleic acid, RNA/DNA hybrid, RNA/chimeric nucleic acid hybrid, chimeric nucleic acid/chimeric nucleic acid hybrid, or chimeric nucleic acid/DNA hybrid, more preferably a single-stranded RNA, single-stranded chimeric nucleic acid, double-stranded RNA, double-stranded chimeric nucleic acid, RNA/DNA hybrid, chimeric nucleic acid/chimeric nucleic acid hybrid, or RNA/chimeric nucleic acid hybrid, even more preferably a double-stranded RNA, double-stranded chimeric nucleic acid, RNA/DNA hybrid, RNA/chimeric nucleic acid hybrid, chimeric nucleic acid/chimeric nucleic acid hybrid, or chimeric nucleic acid/DNA hybrid, especially a double-stranded RNA.

d. "miR582" Molecule

RNA (formula (I)) of double-stranded form constructed from a nucleic acid comprising a nucleotide sequence represented by SEQ ID NO: 1 and a nucleic acid comprising a nucleotide sequence represented by SEQ ID NO: 2 is known as "mature miR582" (Non-patent Reference 3).

[Chemical Formula 1]
Formula (I)

(SEQ ID NO: 1)
5'-UUACAGUUGUUCAACCAGUUACU-3'

3'-CCAAGUCAACAAGUUGGUCAAU-5' (SEQ ID NO: 2)

Therefore, the active ingredient of this embodiment may be the above mature miR582.

e. Precursors of "miR582"

The active ingredient of this embodiment may also be a precursor of miR582. A precursor of miR582 means a nucleic acid capable of producing mature miR582 inside a cell as a result of intracellular processing and cleavage of double-stranded nucleic acid. Examples include pri-miRNA and pre-miRNA of miR582 and the like. pri-miRNA is a primary transcript (single-stranded RNA) of an miRNA gene and usually has a length of about several hundred to several thousand bases. pre-miRNA is single-stranded RNA having a hairpin structure produced by intracellular processing of pri-miRNA and usually has a length of 90-110 bases. pri-miRNA and pre-miRNA of miR582 are known molecules and are disclosed, for example, in the miRBase database: http://microrna.sanger.ac.uk/ created by the Sanger Institute. A single-stranded RNA comprising a nucleotide sequence known as "MI0003589" can be given as an example of a suitable pre-miRNA of miR582.

As one that takes on a structure similar to pre-miRNA, one preferred embodiment of the nucleic acid of this embodiment is a single-stranded nucleic acid in which a nucleotide sequence represented by SEQ ID NO: 1 or SEQ ID NO: 2 (first sequence) and a complementary sequence thereof (second sequence) are linked, and the nucleic acid has the form of a double-stranded construct of the first sequence and second sequence by taking on the structure of a hairpin loop. To explain this taking the above "MI0003589" as an example, a preferred nucleic acid in this embodiment may take on a structure represented by the following formula (II) (SEQ ID NO: 3).

[Chemical Formula 2]

Formula (II)

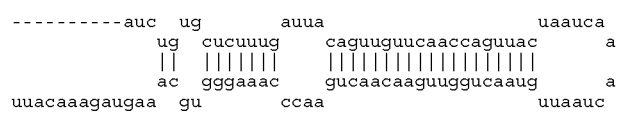

The nucleic acid of this embodiment can be obtained by production by conventional, known methods by isolation from mammalian cells (human cells and the like), by chemical synthesis, and by using recombinant DNA technology. Suitable commercially available nucleic acids can also be used. One such commercial product can be purchased as "Human miRIDIAN microRNA Mimic (product name, Dharmacon).

f. Modified Nucleic Acids

The native nucleic acid can sometimes be degraded easily by nucleolytic enzymes present within the cell. Therefore, nucleic acids of this embodiment also include nucleic acids that have been modified so as to resist various types of lytic enzymes (also called "modified form" hereinafter) (see, for example, Curr. Top. Med. Chem., 6: 913-25 (2006) and Mol. Biosyst., 6: 862-70 (2010)). Specifically, any one of the above nucleic acids that have been modified so that none of the desired bioactivities of the present invention discussed below have always been compromised are included in nucleic acids of this embodiment. Examples of these modified forms include, but are not limited to, those having a modified sugar chain moiety (for example, 2'-O methylation), those having a modified base moiety, those having a modified phosphate moiety or hydroxyl moiety (for example, biotin, amino group, lower alkylamine group, acetyl group, and the like). The nucleic acid itself may also be modified. Examples of modification of the nucleic acid itself include addition of cholesterol, vitamin, or another such fatty substance or a fluorescent substance at the 5' end or 3' end. Another example may be a synthetic nucleic acid containing an identical region to miR582 and a complementary region that is from 60% to less than 100% complementary with that sequence. Alternatively, it may be a synthetic RNA molecule as described in the PCT WO2006/627171 pamphlet.

Nucleic acids in this embodiment may also have additional bases at the 5' or 3' end. The length of these additional bases is usually 5 or fewer. These additional bases may be DNA or RNA, but the stability of the nucleic acid can sometimes be improved when DNA is used. Examples of such additional base sequences include, but are not limited to, ug-3', uu-3', tg-3', tt-3', ggg-3', guuu-3', gttt-3', ttttt-3', uuuuu-3', and other such sequences.

Examples of preferred embodiments of the nucleic acid of this embodiment include nucleic acid comprising SEQ ID NO: 1 or SEQ ID NO: 2, mature miR582, a precursor thereof, and other such nucleic acids. A nucleic acid containing a nucleotide having mature miR582 activity, for example, "miR582 mimicHuman miRIDIAN microRNA Mimic" (product name, Dharmacon), synthesized to mimic endogenous mature miR582, and the like can also be used as another embodiment of the nucleic acid of this embodiment. Other examples include Pre-miR™ miRNA precursor molecule (manufactured by Life Technologies).

g. Activity of Nucleic Acid

When taken up into a cancer cell, the nucleic acid in this embodiment can demonstrate suppressive activity on cancer cell invasion and growth and can act to suppress cancer cell metastasis. These actions are thought to derive from the fact that the nucleic acid of this embodiment has protein expression-suppressing activity. Therefore, the nucleic acid of this embodiment must have at least protein expression-suppressing activity. Suppressing the expression of the target mRNA (this action is also sometimes called RNA expression-suppressing activity) and inhibiting the translation of the target mRNA are included in protein expression suppression. Degradation of the target mRNA produced by transcription, resulting in a decrease in the expression level of the target mRNA is included in the above suppression of expression of the target mRNA. More specifically, in this embodiment, a "nucleic acid having miR582 activity" is preferably used in a medicine of this embodiment. Here, "miR582 activity" is activity for suppressing the expression of at least one of the proteins related to mRNA that can serve as a target for any native "miR582" molecule, meaning activity for suppressing expression of at least one of these mRNAs as a typical example. However, the "nucleic acid having miR582 activity" of this embodiment should be a nucleic acid that suppresses the expression of at least one of the proteins related to the target mRNA of the native "miR582" molecule or suppresses the expression of at least one of these mRNAs. Examples of target mRNAs the expression of which are suppressed by native "miR582" include PGGT1B (Gene ID 5229), LRRK2 (Gene ID 120892), DIXDC1 (Gene ID 85458), RAB27A (Gene ID 5873), KCNC1 (Gene ID 3746), TEX19 (Gene ID 400629), or ASGR1 (Gene ID 432).

Therefore, concrete examples of the "nucleic acid having miR582 activity" of this embodiment can be nucleic acids having KCNC1, PGGT1B, LRRK2, DIXDC1, RAB27A, and the like as the target mRNAs that suppress their expression. These "nucleic acid having miR582 activity" preferably suppress the expression of LRRK2, more preferably suppress the expression of LRRK2 and DIXDC1, even more preferably suppress the expression of LRRK2, DIXDC1, and RAB27A, even more preferably suppress the expression of LRRK2, DIXDC1, RAB27A, and PGGT1B, and ideally suppress the expressions of LRRK2, DIXDC1, RAB27A, PGGT1B, and KCNC1.

To give a more specific embodiment, the nucleic acid is preferably miR582 and it preferably suppresses the expression of PGGT1B in this embodiment. In addition, the expression of PGGT1B and LRRK2 is more preferably suppressed, the expression of PGGT1B, LRRK2, and DIXDC1 is even more preferably suppressed, the expressions of PGGT1B, LRRK2, DIXDC1, and RAB27A are even more preferably suppressed, and the expressions of PGGT1B, LRRK2, DIXDC1, RAB27A, and KCNC1 are ideally suppressed using miR582. In another specific embodiment, the expression of LRRK2 is preferably suppressed, the expressions of LRRK2 and DIXDC1 are more preferably suppressed, the expressions of LRRK2, DIXDC1, and RAB27A are even more preferably suppressed, and the expressions of LRRK2, DIXDC1, RAB27A, and KCNC1 are especially preferably suppressed using miR582-5p as the nucleic acid. In another specific embodiment, the expression of LRRK2 is preferably suppressed, the expression of LRRK2 and DIXDC1 is more preferably suppressed, and the expression of LRRK2, DIXDC1, and KCNC1 is ideally suppressed using miR582-3p as the nucleic acid.

Furthermore, a "nucleic acid having miR582 activity" of this embodiment may suppress the function of a target protein of miR582 in addition to suppressing the expression of a target mRNA or suppressing the translation of a target mRNA as the mechanism of suppressing the expression of at least one of the proteins related to the target mRNAs of miR582. In short, the nucleic acid of this embodiment may substantially suppress the expression of a protein related to the target mRNA of miR582, the expression of this mRNA, or the like. For example, if a nucleic acid of this embodiment suppresses the expression of a protein related to a target mRNA or this mRNA by at least 10% or more, this nucleic acid can be regarded as having substantially suppressed the expression of the protein related to the target mRNA or this mRNA. The nucleic acid in this embodiment preferably suppresses the expression of a protein related to a target mRNA of miR582 or this mRNA 20% or more, more preferably 30% or more, even more preferably 40% or more, especially preferably 50% or more, and ideally 60% or more. The ability to suppress expression can be confirmed by the methods described in any one of Examples 7 to 9 in this specification.

On the other hand, it can also be called a necessary and sufficient condition that the "nucleic acid having miR582 activity" of this embodiment substantially form a hybrid with at least one of the target mRNA of native miR582. For example, if the "nucleic acid having miR582 activity" of this embodiment can form a hybrid with at least one of the target mRNA at 25° C. in 0.1M phosphate buffer (pH 7.0), this nucleic acid can be regarded as having substantially formed a hybrid with at least one of the target mRNA. Examples of target mRNA with which native miR582 forms a hybrid include PGGT1B, LRRK2, DIXDC1, and RAB27A.

Therefore, a "nucleic acid having miR582 activity" of this embodiment preferably forms a hybrid with PGGT1B, more preferably forms a hybrid with PGGT1B and DIXDC1, even more preferably forms a hybrid with PGGT1B, DIXDC1, and LRRK2, and ideally forms a hybrid with PGGT1B, DIXDC1, LRRK2, and RAB27A.

To give a more specific embodiment, the nucleic acid of this embodiment is preferably miR582-5p or miR582 and these preferably form a hybrid with PGGT1B, more preferably form a hybrid with PGGT1B and DIXDC1, even more preferably form a hybrid with PGGT1B, DIXDC1, and LRRK2, and ideally form a hybrid with PGGT1B, DIXDC1, LRRK2, and RAB27A. In another embodiment, the nucleic acid is preferably miR582-3p and it preferably forms a hybrid with PGGT1B, more preferably forms a hybrid with PGGT1B and DIXDC1, even more preferably forms a hybrid with PGGT1B, DIXDC1, and LRRK2. Furthermore, the ability to form a hybrid can be confirmed, for example, by the methods described in Examples 6 to 8 in this specification.

h. Targets of Treatment/Prevention

The cancer cells that are the targets of treatment in this embodiment are usually cancer cells of mammals (for example, rats, mice, guinea pigs, rabbits, sheep, horses, pigs, cows, monkeys, humans, preferably humans). The type of cancer is not particularly restricted as long as the cancer is one in which the expression of miR582 is decreased; examples include bladder cancer, breast cancer, lung cancer, lung tumor, prostate cancer, osteosarcoma, esophageal cancer, liver cancer, stomach cancer, colorectal cancer, rectal cancer, colon cancer, ureteral tumors, brain tumors, gall bladder cancer, bile duct cancer, biliary tract cancer, kidney cancer, ovarian cancer, cervical cancer, thyroid cancer, testicular tumors, Kaposi's sarcoma, maxillary cancer, tongue cancer, lip cancer, cancer of the oral cavity, laryngeal cancer, pharyngeal cancer, myosarcoma, skin cancer, and other such solid cancers, myeloma, leukemia, and the like. Bladder cancer is preferred as the cancer that is the target of treatment, and metastatic bladder cancer is more preferred. Grade 2 or grade 3 bladder cancer is preferred, and grade 2 bladder cancer is more preferred as the bladder cancer that is the target of treatment. Grade 3 bladder cancer can also be treated suitably as an embodiment.

To give a more specific embodiment, whether or not a medicine of this embodiment has activity for inhibiting cancer cell growth may be checked by using cancer cell lines of the above targets of treatment/prevention. In particular, whether or not a medicine of this embodiment has activity for inhibiting bladder cancer cell growth may be checked by using a bladder cancer cell line such as the UM-UC-3 cells described in Example 3 and Example 5 in this specification. Moreover, whether or not a medicine of this embodiment has activity for inhibiting the invasive capacity of cancer cells may be checked by using highly invasive bladder cancer cells such as the UM-UC-3 cells described in Example 4 and Example 5 in this specification.

i. Medicine

The medicine of this embodiment can contain any carriers, for example, pharmaceutically acceptable carriers, in addition to an effective dose of the nucleic acid of this embodiment and can be used as a medicine in the form of a pharmaceutical composition.

Examples of pharmaceutically acceptable carriers include, but are not limited to, sucrose, starch, and other such excipients; cellulose, methyl cellulose, and other such binders; starch, carboxymethyl cellulose, and other such disintegrating agents; magnesium stearate, Aerosil, and other such lubricants; citric acid, menthol, and other such flavoring agents; sodium benzoate, sodium bisulfite, and other such preservatives; citric acid, sodium citrate, and other such stabilizers; methyl cellulose, polyvinyl pyrrolidone, and other such suspending agents; surfactants and other such dispersing agents; water, physiological saline, and other such diluents; beeswax, and the like.

To accelerate introduction of the nucleic acid of this embodiment into cancer cells, the medicine of this embodiment can also contain a reagent for nucleic acid introduction. Atelocollagen; liposomes; nanoparticles; lipofectin, lipofectamine, DOGS (transfectam), DOPE, DOTAP, DDAB, DHDEAB, HDEAE, polybrene, poly(ethyleneimine), and other such cationic lipids, and the like can be used as reagents for nucleic acid introduction.

Compounding the medicine of this embodiment with atelocollagen can cause the nucleic acid of this embodiment to reach to the target cancer cells efficiently and cause it to be taken up efficiently by the cells.

The agent of the present invention can be administered to a mammal orally or parenterally. It is preferable, however, to administer the agent of the present invention parenterally.

Formulations suited to parenteral administration (for example, subcutaneous injections, intramuscular injections, local injections, intraperitoneal injections, and the like) are aqueous and nonaqueous isotonic sterile injection solutions. These may contain antioxidants, buffers, bacteriostatics, isotonifying agents, and the like. Examples also include aqueous and nonaqueous sterile suspensions. These may contain suspending agents, solubilizing agents, thickeners, stabilizers, preservatives, and the like. Unit dosages or multiple dosages of these formulations can be sealed in a container such as an ampule or vial. The active ingredient and pharmaceutically acceptable carrier can also be freeze dried and stored in a form that may be dissolved or suspended in a suitable sterile vehicle immediately before use. Examples of other formulations suited to parenteral administration include sprays and the like. A local injection to be administered transurethrally is also preferred as a formulation for use in the treatment of bladder cancer.

The content of the nucleic acid of this embodiment in the pharmaceutical composition is, for example, approximately 0.1 to 100 wt % of the total pharmaceutical composition.

The dose of the medicine of this embodiment varies depending on the goal of administration, method of administration, type of cancer, size, and state of the subject being administered (gender, age, weight, and the like), but from 1 pmol/kg to 10 nmol/kg in local administration for injection to an adult and from 2 nmol/kg to 200 nmol/kg in systemic administration is usually preferred as the amount of nucleic acid. Such doses are preferably administered 1-10 times, more preferably 5-10 times.

The medicine of this embodiment is administered safely to a mammal (for example, a rat, mouse, guinea pig, rabbit, sheep, horse, pig, cow, monkey, or human) so that the nucleic acid of this embodiment which is the active ingredient reaches the cancer tissue (cancer cells).

The nucleic acid of this embodiment has activity for suppressing cancer cell growth. A cancer condition can be treated by administering a medicine of this embodiment to a cancer patient or the like. The nucleic acid of this embodiment also preferably has activity for inhibiting the invasive capacity of cancer cells. Cancer invasion and metastasis can be suppressed and conditions caused by the invasion and metastasis of cancer can be treated or prevented by administering a medicine of this embodiment to a cancer patient, a patient who is at risk for metastasis after cancer treatment, and the like. Therefore, the medicine of this embodiment is highly useful as an agent for treating cancer.

Furthermore, "metastasis suppression" means suppression of secondary occurrence of a tumor at that site when tumor cells move from the primary focus to another site.

As mentioned above, cancers in which the medicine of this embodiment can be used are not particularly restricted as long as it is a cancer in which the expression of miR582 is decreased. Examples include breast cancer, lung cancer, lung tumor, prostate cancer, osteosarcoma, esophageal cancer, liver cancer, stomach cancer, colorectal cancer, rectal cancer, colon cancer, ureteral tumors, brain tumors, gall bladder cancer, bile duct cancer, biliary cancer, kidney cancer, bladder cancer, ovarian cancer, cervical cancer, thyroid cancer, testicular tumors, Kaposi's sarcoma, maxillary cancer, tongue cancer, lip cancer, cancer of the oral cavity, laryngeal cancer, pharyngeal cancer, myosarcoma, skin cancer, retinoblastoma, and other such solid cancers; myeloma, leukemia, malignant lymphoma, myeloma, malignant melanoma, hemangioma, polycythemia vera, neuroblastoma, and the like. Bladder cancer and metastatic cancer can be given as preferred examples of the use of the medicine of this embodiment.

Metastatic cancers include breast cancer, lung cancer, lung tumor, prostate cancer, kidney cancer, multiple myeloma, thyroid cancer, adenocarcinoma, blood cell malignant tumors including leukemia and lymphoma; cancers of the head and neck; cancers of the digestive tract including stomach cancer, colon cancer, colorectal cancer, and liver cancer; malignant tumors of the female reproductive organs including ovarian cancer, endometrial cancer, and cervical cancer; bladder cancer; brain tumors including neuroblastoma; sarcoma, osteosarcoma; skin cancers including malignant melanoma and squamous cell carcinoma; and other such metastatic cancers. Metastatic bladder cancer can be given as a preferred example of the use of the medicine of this embodiment. Examples of conditions caused by cancer metastasis include respiratory failure due to metastatic cancers, tumor enlargement and carcinomatous pleurisy, and the like.

The medicine in this embodiment can be used in conjunction with other anticancer agents. Examples of other anticancer agents include not only taxanes and other such microtubule agonists, but also metabolic antagonists, DNA alkylating agents, DNA binding agents (platinum formulations), anticancer antibiotics, and the like. Specific examples include amrubicin hydrochloride, irinotecan hydrochloride, ifosfamide, etoposide Lastet, gefinitib, cyclophosphamide, cisplatin, trastuzumab, fluorouracil, mitomycin C, imatinib mesilate, methotrexate, Rituxan, Adriamycin, and the like.

2. Method for Predicting the Therapeutic Effect of a Medicine of this Embodiment An example of this embodiment is a method for measuring the expression level of miR582 in a cancer and predicting the therapeutic effect of a medicine of this embodiment or assisting a physician in making this prediction based on the fact that this expression level is decreased in cancer in comparison to normal tissue (both of these methods are collectively termed "prediction method" hereinafter).

In the prediction method of this embodiment, the expression level of miR582 is measured in cancer tissue or cancer cells excised from a patient who is the subject of measurement prior to administration of a medicine of this embodiment. The expression level of miR582 can also be estimated by measuring the copy number of the chromosomal region of miR582 as in Example 2 in this specification. The cancers detailed above in section "h. Targets of treatment/prevention" can be given as examples of the types of cancer on which the prediction method of this embodiment can be used. The prediction method of this embodiment can preferably be applied to bladder cancer.

The miR582 the expression level of which is measured in the prediction method of this embodiment includes a nucleotide sequence represented by SEQ ID NO: 1 or SEQ ID NO: 2, mature miR582, pri-miRNA, and pre-miRNA, but preferably the total expression level of all of these forms or the expression level of a nucleotide sequence represented by SEQ ID NO: 1 or SEQ ID NO: 2 or the mature form, or more preferably the expression level of a nucleotide sequence represented by SEQ ID NO: 1 or SEQ ID NO: 2, is measured.

The expression level of miR582 can be measured, for example, by methods known per se using a nucleic acid probe capable of specifically detecting this miRNA. Examples of measurement methods include RT-PCR, northern blotting, in situ hybridization, nucleic acid array, and the like. Measurement is also possible by a commercial kit (for example, a TaqMan(registered trade mark) MicroRNA Cells-to-CT kit).

Examples of nucleic acid probes capable of specifically detecting miR582 include polynucleotides containing 15 bases or more, preferably 18 bases or more, more preferably approximately 20 bases or more, and ideally the entire length of the successive nucleotide sequence contained in a nucleotide sequence represented by SEQ ID NO: 1 or SEQ ID NO: 2, or a complementary sequence thereof. Similarly, examples of nucleic acid probes capable of detecting nucleic acid having miR582 activity include polynucleotides containing 15 bases or more, preferably 18 bases or more, more preferably approximately 20 bases or more, and ideally the entire length of the successive nucleotide sequence contained in a nucleotide sequence represented by SEQ ID NO: 1 or SEQ ID NO: 2, or a complementary sequence thereof.

The nucleic acid probe may contain additional sequences (nucleotide sequences not complementary with the polynucleotide that is to be detected) within the range that does not interfere with specific detection. The nucleic acid probe may also be labeled by a suitable label, for example, a radioisotope (e.g., $^{125}I$, $^{131}I$, $^{3}H$, $^{14}C$, or the like), enzyme (e.g., β-galactosidase, β-glucosidase, alkaline phosphatase, peroxidase, malic dehydrogenase, and the like), fluorescent substance (e.g., fluorescamine, fluorescein isothiocyanate, and the like), luminescent substance (e.g., luminol, luminol derivative, luciferrin, lucigenin, and the like), and the like. Alternatively, a quencher that absorbs fluorescent energy generated by a fluorescent substance may also be bonded in the vicinity of the fluorescent substance (e.g., FAM, VIC, or the like). In such embodiments, the fluorescent substance and quencher are separated during the detection reaction, and the fluorescence is detected.

The nucleic acid probe may be any one of DNA, RNA, or chimeric nucleic acid, and may be single-stranded or double-stranded. Nucleic acid probes or primers can be synthesized, for example, by the usual methods using automated DNA/RNA synthesis equipment based on the information of the nucleotide sequence represented by SEQ ID NO: 1, SEQ ID NO: 2, or a sequence complementary thereto.

The therapeutic effect on the cancer is predicted based on the expression level of miR582 measured as described above. As will be shown in the examples below, the expression level of miR582 is lower in bladder cancer than in normal bladder tissue. The above prediction is therefore made based on a difference in the expression level of miR582 in bladder cancer and normal tissue.

For example of the prediction of this embodiment, cancer tissue is excised (or cancer cells are obtained) from a bladder cancer patient prior to conducting anticancer treatment, and the expression level of miR582 is compared in noncancerous tissue surrounding the cancer tissue and in the cancer tissue. The comparison of the expression level is preferably based on the existence of a significant difference. When the results of the comparison of the miR582 expression levels indicate that the expression level of miR582 is relatively low in the cancer tissue, one can predict that cancer treatment using miR582 or a nucleic acid having miR582 activity or anticancer treatment to raise the expression level of miR582 will be effective. Conversely, when the expression level of miR582 to be measured is relatively high, one can predict that cancer treatment using miR582 or a nucleic acid having miR582 activity or anticancer treatment to raise the expression level of miR582 will not be effective.

Since bladder cancer patients having a decreased expression level of miR582 in the cancer tissue (or cancer cells) are preferred as the targets of treatment of the medicine of this embodiment, the prediction method of this embodiment can be used to select patients in whom the medicine of this embodiment can be expected to have a therapeutic effect, especially bladder cancer patients. Specifically, patients having an expression level of miR582 in the cancer tissue (or cancer cells) of 75% or less, preferably 50% or less, and more preferably 25% or less, as compared to the expression level of miR582 in normal cells are preferred as patients to be selected by the prediction method of this embodiment.

In the same way, the prediction method of this embodiment can also be carried out by comparing the copy number of the genomic region of miR582 in cancer tissue and surrounding noncancerous normal tissue excised from a bladder cancer patient and estimating the expression level of miR582. The comparison of the copy number of the genomic region of miR582 is preferably based on the existence of a significant difference. When the results of the comparison of the copy number of the genomic region of miR582 indicate that the copy number of the genomic region of miR582 to be measured is relatively less in the cancer tissue than in the normal tissue, one can predict that this is cancer tissue in which there will be a significant therapeutic effect. Conversely, when the copy number of the genomic region of miR582 to be measured is equal to or greater than that of the normal tissue even in the cancer tissue, one can predict that this is cancer tissue in which there will be little therapeutic effect.

Specifically, the copy number of the genomic region of miR582 in the cancer tissue (or cancer cells) is 75% or less, preferably 50% or less, and more preferably 25% or less, as compared to the copy number of the genomic region of miR582 in normal cells is preferred as a subject for treatment by the medicine of this embodiment.

As is evident from the above explanation, this embodiment provides a composition (sometimes referred to as the "composition of this embodiment" hereinafter) for predicting the therapeutic effect of a medicine of this embodiment, including nucleic acid probes capable of specifically detecting miR582 or nucleic acid having miR582 activity as described above. The composition of this embodiment can be a kit for predicting the therapeutic effect of an anticancer agent. The use of a composition of this embodiment makes it possible to predict the therapeutic effect of a medicine of this embodiment easily by the above prediction method.

Nucleic acid probes in the usual form of an aqueous solution dissolved to make a suitable concentration in water or a suitable buffer (e.g., TE buffer, PBS, or the like) or nucleic acid probes in the form of a nucleic acid array immobilized on a solid support are included in the composition of this embodiment.

The composition of this embodiment may also contain as a constituent other components necessary to carry out the method in accordance with the method for measuring miR582 or nucleic acid having miR582 activity. For example, in the case of measurement using northern blotting or nucleic acid array, the composition of this embodiment can also contain blotting buffer, labeling reagent, blotting membrane, and the like. When in situ hybridization is used in measurement, the composition of this embodiment can also contain labeling reagent, chromogenic substrate, and the like.

3. Method for Assessing the Therapeutic Effect of a Medicine of this Embodiment

An example of this embodiment is a method for measuring the expression level of miR582 in a cancer and assessing the therapeutic effect of a medicine of this embodiment or assisting a physician in making this assessment based on the fact that this expression level is decreased in cancer in comparison to normal tissue (both of these methods are collectively termed "assessment method" hereinafter).

In the assessment method of this embodiment, the expression level of miR582 is measured in cancer tissue or cancer cells excised from a patient who is the subject of measurement. The expression level of miR582 can also be estimated by measuring the copy number of the chromosomal region of miR582 as in Example 2 below. The cancers detailed above in section "h. Targets of treatment/prevention" can be given as examples of the types of cancer on which the assessment method of this embodiment can be used. The assessment method of this embodiment can preferably be applied to bladder cancer.

The miR582 the expression level of which is measured in the assessment method of this embodiment includes a nucleotide sequence represented by SEQ ID NO: 1 or SEQ ID NO: 2, mature miR582, pri-miRNA, and pre-miRNA, but preferably the total expression level of all of these forms or the expression level of a nucleotide sequence represented by SEQ ID NO: 1 or SEQ ID NO: 2 or the mature form, or more preferably the expression level of a nucleotide sequence represented by SEQ ID NO: 1 or SEQ ID NO: 2, is measured.

The expression level of miR582 can be measured, for example, by methods known per se using a nucleic acid probe capable of specifically detecting this miRNA. Examples of measurement methods include RT-PCR, northern blotting, in situ hybridization, nucleic acid array, and the like. Measurement is also possible by a commercial kit (for example, a TaqMan(registered trade mark) MicroRNA Cells-to-CT kit).

Examples of nucleic acid probes capable of specifically detecting miR582 include polynucleotides containing 15 bases or more, preferably 18 bases or more, more preferably approximately 20 bases or more, and ideally the entire length of the successive nucleotide sequence contained in the nucleotide sequence represented by SEQ ID NO: 1 or SEQ ID NO: 2, or a complementary sequence thereof. Similarly, examples of nucleic acid probes capable of detecting nucleic acid having miR582 activity include polynucleotides containing 15 bases or more, preferably 18 bases or more, more preferably approximately 20 bases or more, and ideally the entire length of the successive nucleotide sequence contained in the nucleotide sequence represented by SEQ ID NO: 1 or SEQ ID NO: 2, or a complementary sequence thereof.

The nucleic acid probe may contain additional sequences (nucleotide sequences not complementary with the polynucleotide that is the subject of detection) within the range that does not interfere with specific detection. The nucleic acid probe may also be labeled by a suitable label, for example, a radioisotope (e.g., $^{125}$I, $^{131}$I, $^{3}$H, $^{14}$C, or the like), enzyme (e.g., β-galactosidase, β-glucosidase, alkaline phosphatase, peroxidase, malic dehydrogenase, and the like), fluorescent substance (e.g., fluorescamine, fluorescein isothiocyanate, and the like), luminescent substance (e.g., luminol, luminol derivative, luciferrin, lucigenin, and the like), and the like. Alternatively, a quencher that absorbs fluorescent energy generated by a fluorescent substance may also be bonded in the vicinity of the fluorescent substance (e.g., FAM, VIC, or the like). In such embodiments, the fluorescent substance and quencher are separated during the detection reaction, and the fluorescence is detected.

The nucleic acid probe may be any one of DNA, RNA, or chimeric nucleic acid, and may be single-stranded or double-stranded. Nucleic acid probes or primers can be synthesized, for example, by the usual methods using automated DNA/RNA synthesis equipment based on the information of the nucleotide sequence represented by SEQ ID NO: 1, SEQ ID NO: 2, or a sequence complementary thereto.

The therapeutic effect on the cancer is assessed based on the expression level of miR582 measured as described above. As will be shown in the examples below, the expression level of miR582 is lower in bladder cancer than in normal bladder tissue. The above assessment is therefore made based on a difference in the expression level of miR582 in bladder cancer and normal tissue.

For example, the assessment method of this embodiment can be carried out by excising cancer tissue (or obtaining cancer cells) from a bladder cancer patient prior to conducting anticancer treatment, and comparing the expression level of miR582 in cancer tissue excised after the same patient has undergone anticancer treatment with noncancerous tissue surrounding the cancer tissue (negative control) and cancer tissue (positive control). The comparison of the expression level is preferably based on the existence of a significant difference. When the results of the comparison of the miR582 expression levels indicate that treatment has relatively raised the miR582 expression level of the subject of measurement in comparison to before treatment, one can assess that the anticancer treatment performed is effective. Conversely, when the expression level of miR582 to be measured becomes relatively lower, one can assess that the anticancer treatment performed is not effective.

Specifically, for example, the expression level of miR582 in the cancer tissue (or cancer cells) prior to anticancer treatment is 75% or less, preferably 50% or less, and more preferably 25% or less as compared to the expression level of miR582 in normal cells when the anticancer treatment performed is assessed to be effective. In addition, the expression level of miR582 in the cancer tissue (or cancer cells)

after cancer treatment is, for example, 125% or more, preferably 150% or more, and even more preferably 200% or more in comparison to the expression level of miR582 in the cancer tissue (or cancer cells) prior to cancer treatment.

In the same way, the prediction method of this embodiment can also be carried out by comparing the copy number of the genomic region of miR582 in cancer tissue excised from a bladder cancer patient prior to conducting anticancer treatment and in cancer tissue after anticancer treatment has been conducted and estimating the expression levels. The comparison of the copy number of the genomic region of miR582 is preferably based on the existence of a significant difference. When the results of the comparison of the copy number of the genomic region of miR582 indicate that the copy number of the genomic region of miR582 to be measured is relatively less in the cancer tissue after anticancer treatment has been conducted than in the cancer tissue prior to conducting anticancer treatment, one can assess that this is cancer tissue in which there is little therapeutic effect. Conversely, when the copy number of the genomic region of miR582 to be measured in cancer tissue after anticancer treatment has been conducted is equal to or greater than that in cancer tissue prior to conducting anticancer treatment, one can predict that this is cancer tissue in which there is a significant therapeutic effect.

Specifically, the copy number of the genomic region of miR582 in the cancer tissue (or cancer cells) prior to anticancer treatment is 75% or less, preferably 50% or less, and more preferably 25% or less as compared to the copy number of the genomic region of miR582 in normal cells when the anticancer treatment conducted is assessed as effective. In addition, the copy number of the genomic region of miR582 in the cancer tissue (or cancer cells) after cancer treatment is 125% or more, preferably 150% or more, and even more preferably 200% or more in comparison to the copy number of the genomic region in the cancer tissue (or cancer cells) prior to cancer treatment.

When miR582 or a nucleic acid having miR582 activity has been administered as an anticancer agent, the therapeutic effect can also be assessed by measuring the amount of miR582 or nucleic acid having miR582 activity in the same way in the administered cancer tissue and comparing it with the expression of miR582 in the cancer tissue prior to administration. Specifically, the anticancer treatment conducted can be assessed to be effective when an increase is found in the amount of miR582 or nucleic acid having miR582 activity in the cancer tissue after administration of miR582 or nucleic acid having miR582 activity.

Since bladder cancer patients having a decreased expression level of miR582 in the cancer tissue (or cancer cells) are preferred as the treatment subjects of the medicine in this embodiment, the assessment method of this embodiment is useful for determining patients, especially these bladder cancer patients, in whom a therapeutic effect has been obtained by a medicine of this embodiment.

As is evident from the above explanation. this embodiment provides a composition (sometimes referred to as the "composition of this embodiment" hereinafter) for assessing the therapeutic effect of a medicine of this embodiment, including nucleic acid probes capable of specifically detecting miR582 or nucleic acid having miR582 activity as described above. The composition of this embodiment can be a kit for assessing the therapeutic effect of a medicine of this embodiment. The use of a composition of this embodiment makes it possible to assess the therapeutic effect of a medicine of this embodiment easily by the above assessment method.

Nucleic acid probes in the usual form of an aqueous solution dissolved to make a suitable concentration in water or a suitable buffer (e.g., TE buffer, PBS, or the like) or nucleic acid probes in the form of a nucleic acid array immobilized on a solid support are included in the composition of this embodiment.

The composition of this embodiment may also contain as a configuration other components necessary to carry out the method in accordance with the method for measuring miR582 or nucleic acid having miR582 activity. For example, in the case of measurement using northern blotting or nucleic acid array, the composition of this embodiment can also contain blotting buffer, labeling reagent, blotting membrane, and the like. When in situ hybridization is used in measurement, the composition of this embodiment can also contain labeling reagent, chromogenic substrate, and the like.

4. Method for Assessing the Prognosis of Cancer Treatment

An example of this embodiment is a method for measuring the expression level of miR582 in cancer and assessing the prognosis of cancer treatment or assisting a physician in assessing this prognosis based on the fact that this expression level is decreased in cancer in comparison to normal tissue or measuring the copy number of the genomic region of miR582 and predicting the expression level of miR582 (both of these methods are collectively termed "prognosis assessment method" hereinafter).

In the prognosis assessment method of this embodiment, the expression level of miR582 is measured in cancer tissue or cancer cells of cancer excised from a patient who is the subject of measurement. The expression level of miR582 can also be estimated by measuring the copy number of the chromosomal region of miR582. The cancers detailed above in section "h. Targets of treatment/prevention" can be given as examples of the types of cancer on which the prognosis assessment method of this embodiment can be used. The prognosis assessment method of this embodiment can preferably be applied to bladder cancer.

The miR582 the expression level of which is measured in the assessment method of this embodiment includes a nucleotide sequence represented by SEQ ID NO: 1 or SEQ ID NO: 2, mature miR582, pri-miRNA, and pre-miRNA, but preferably the total expression level of all of these forms or the expression level of a nucleotide sequence represented by SEQ ID NO: 1 or SEQ ID NO: 2 or the mature form, or more preferably the expression level of a nucleotide sequence represented by SEQ ID NO: 1 or SEQ ID NO: 2, is measured.

The expression level of miR582 can be measured, for example, by methods that are themselves known using a nucleic acid probe capable of specifically detecting this miRNA. Examples of measurement methods include RT-PCR, northern blotting, in situ hybridization, nucleic acid array, and the like. Measurement is also possible by a commercial kit (for example, a TaqMan(registered trademark) MicroRNA Cells-to-CT kit).

Examples of nucleic acid probes capable of specifically detecting miR582 include polynucleotides containing 15 bases or more, preferably 18 bases or more, more preferably approximately 20 bases or more, and ideally the entire length of successive nucleotide sequence contained in the nucleotide sequence represented by SEQ ID NO: 1 or SEQ ID NO: 2, or a complementary sequence thereof.

The expression level of miR582 can also be estimated by measuring the copy number of the genomic region that encodes this miRNA.

Examples of nucleic acid probes capable of specifically detecting and permitting measurement of the copy number of the genomic region encoded by miR582 include polynucleotides containing 15 bases or more, preferably 18 bases or more, more preferably approximately 20 bases or more, and ideally the entire length of successive nucleotide sequence contained in a nucleotide sequence represented by SEQ ID NO: 4 or SEQ ID NO: 5 discussed below, or a complementary sequence thereof.

The nucleic acid probe may contain additional sequences (nucleotide sequences not complementary with the polynucleotide that is the subject of detection) within the range that does not interfere with specific detection. The nucleic acid probe may also be labeled by a suitable label, for example, a radioisotope (e.g., $^{125}$I, $^{131}$I, $^{3}$H, $^{14}$C, or the like), enzyme (e.g., β-galactosidase, β-glucosidase, alkaline phosphatase, peroxidase, malic dehydrogenase, and the like), fluorescent substance (e.g., fluorescamine, fluorescein isothiocyanate, and the like), luminescent substance (e.g., luminol, luminol derivative, luciferrin, lucigenin, and the like), and the like. Alternatively, a quencher that absorbs fluorescent energy generated by a fluorescent substance may also be bonded in the vicinity of the fluorescent substance (e.g., FAM, VIC, or the like). In such embodiments, the fluorescent substance and quencher are separated during the detection reaction, and the fluorescence is detected.

The nucleic acid probe may be any one of DNA, RNA, or chimeric nucleic acid, and may be single-stranded or double-stranded. Nucleic acid probes or primers can be synthesized, for example, by the usual methods using automated DNA/RNA synthesis equipment based on the information of the nucleotide sequence represented by SEQ ID NO: 1, SEQ ID NO: 2, SEQ ID NO: 4, SEQ or ID NO: 5.

The prognosis of cancer treatment is assessed based on the expression level of miR582 measured as described above. As will be shown in the examples below, the expression level of miR582 is lower in bladder cancer than in normal bladder tissue. The above prediction is therefore made based on a difference in the expression level of miR582 in bladder cancer and normal tissue or on measuring the copy number of the genomic region of miR582 and estimating the expression level of miR582.

For example, the prognosis assessment method of this embodiment can be carried out by excising cancer tissue (or obtaining cancer cells) from a bladder cancer patient and comparing the expression level of miR582 in noncancerous normal tissue surrounding the cancer and in cancer tissue. The comparison of the expression level is preferably based on the existence of a significant difference. When the results of the comparison of the miR582 expression levels indicate that the expression level of miR582 to be measured is relatively higher in the cancer tissue than in the normal tissue, one can assess that this is cancer tissue having a good prognosis. Conversely, when the expression level of miR582 to be measured is relatively lower, one can assess that this is cancer tissue having a poor prognosis.

Specifically, the expression level of miR582 in the cancer tissue (or cancer cells) assessed to have a poor prognosis is 75% or less, preferably 50% or less, and more preferably 25% or less as compared to the expression level of miR582 in normal cells.

In the same way, the prognosis assessment method of this embodiment can also be carried out by comparing the copy number of the genomic region of miR582 in cancer tissue excised from a bladder cancer patient and in surrounding noncancerous normal tissue and estimating the expression level. The comparison of the copy number of the genomic region of miR582 is preferably based on the existence of a significant difference. When the results of the comparison of the copy number of the genomic region of miR582 indicate that the copy number of the genomic region of miR582 is relatively less in the cancer tissue than in the normal tissue, one can predict a low expression level of miR582 and asses this to be cancer tissue having a poor prognosis. Conversely, when the copy number of the genomic region of miR582 to be measured is equal to or greater than the normal tissue, one can predict a high expression level of miR582 and assess this to be cancer tissue having a good prognosis.

Specifically, the copy number of the genomic region of miR582 in the cancer tissue (or cancer cells) assessed to have a poor prognosis is 75% or less, preferably 50% or less, and more preferably 25% or less as compared to the copy number of the genomic region of miR582 in normal cells.

Since bladder cancer patients having a decreased expression level of miR582 in the cancer tissue (or cancer cells) are preferred as the treatment subjects of the medicine of this embodiment, the prognosis assessment method of this embodiment is useful for determining patients, especially these bladder cancer patients, for whom treatment by a medicine of this embodiment holds a good prognosis.

As is evident from the above explanation, this embodiment provides a composition (sometimes referred to as the "composition of this embodiment" hereinafter) for assessing the prognosis of cancer treatment, including nucleic acid probes capable of specifically detecting miR582 or nucleic acid probes capable of specifically detecting the genomic region of miR582 and measuring the copy number thereof as described above. The composition of this embodiment can be a kit for assessing the prognosis of cancer treatment. The use of a composition of this embodiment makes it possible to assess the prognosis of cancer treatment easily by the above assessment method.

Nucleic acid probes in the usual form of an aqueous solution dissolved to make a suitable concentration in water or a suitable buffer (e.g., TE buffer, PBS, or the like) or nucleic acid probes in the form of a nucleic acid array immobilized on a solid support are included in the composition of this embodiment.

The composition of this embodiment may also contain as a configuration other components necessary to carry out the method in accordance with the method for measuring miR582 or nucleic acid having miR582 activity. For example, in the case of measurement using northern blotting or nucleic acid array, the composition of this embodiment can also contain blotting buffer, labeling reagent, blotting membrane, and the like. When in situ hybridization is used in measurement, the composition of this embodiment can also contain labeling reagent, chromogenic substrate, and the like.

5. Method for Screening Substances Capable of Suppressing the Growth of Bladder Cancer, Substances Capable of Inhibiting Cancer Metastasis or the Invasive Capacity of Cancer Cells, and the Like.

Examples of this embodiment are a method for screening substances for suppressing the growth of cancer and substances capable of inhibiting the metastasis of cancer or the invasive capacity of cancer, including an evaluation of whether or not a test substance potentiates the expression of miR582, and substances that can be obtained by these methods. In the screening method of this embodiment, substances that upregulate the expression of miR582 are selected as substances capable of suppressing the growth of cancer and substances capable of inhibiting the metastasis of cancer or the invasive capacity of cancer cells.

Test substances provided for the screening method of this embodiment may be any known compounds and novel compounds. Examples include nucleic acids, carbohydrates, lipids, proteins, peptides, organic low-molecular compounds, compound libraries created using combinatorial chemistry technology, random peptide libraries, natural components derived from microorganisms, plants and animals, marine life, and the like.

The method for screening substances capable of suppressing the growth of cancer of this embodiment includes the following steps (1)-(3):

(1) a step for bringing a test substance and cells that permit measurement of the expression of a nucleic acid according to SEQ ID NO: 1 or SEQ ID NO: 2 into contact, (2) a step for measuring the expression level of a nucleic acid according to SEQ ID NO: 1 or SEQ ID NO: 2 in cells that have been brought into contact with the test substance and comparing the expression level with the expression level of a nucleic acid according to SEQ ID NO: 1 or SEQ ID NO: 2 in control cells that have not been brought into contact with the test substance, and (3) a step for selecting a test substance that upregulates the expression level of a nucleic acid according to SEQ ID NO: 1 or SEQ ID NO: 2 as a substance capable of inhibiting the growth of cancer based on the results of comparison in (2) above.

The method for screening substances capable of inhibiting the metastasis of cancer or the invasive capacity of cancer cells of this embodiment also includes the following steps (1)-(3):

(1) a step for bringing a test substance and cells that permit measurement of the expression of a nucleic acid according to SEQ ID NO: 1 or SEQ ID NO: 2 into contact, (2) a step for measuring the expression level of a nucleic acid according to SEQ ID NO: 1 or SEQ ID NO: 2 in cells that have been brought into contact with the test substance and comparing the expression level with the expression level of a nucleic acid according to SEQ ID NO: 1 or SEQ ID NO: 2 in control cells that have not been brought into contact with the test substance, and (3) a step for selecting a test substance that upregulates the expression level of a nucleic acid according to SEQ ID NO: 1 or SEQ ID NO: 2 as a substance capable of inhibiting the metastasis of cancer or the invasive capacity of cancer based on the results of comparison in (2) above.

Mature miR582, pri-miRNA, and pre-miRNA are included in the nucleic acid according to SEQ ID NO: 1 or SEQ ID NO: 2 the expression level of which is measured in the screening method of this embodiment. Preferably, the total expression level of all of these forms or the expression level of the mature form, more preferably the expression level of the mature form, is measured.

The phrase "cells that permit measurement of the expression" means cells that make it possible to evaluate the expression level of the miRNA to be measured. Examples of these cells are cells capable of expressing the miRNA to be measured in nature.

Cells to be measured, i.e. cells capable of expressing miR582 in nature, are not particularly restricted as long as they potentially express miR582. First-generation cultured cells of mammals (for example, humans, mice, and the like), cell lines derived from these first-generation cultured cells, and the like can be used as these cells. Cells of cancers detailed above in section "h. Targets of treatment/prevention" can be given as examples of cells capable of expressing miR582 in nature. These are preferably bladder cancer cells, more preferably highly metastatic or invasive bladder cancer cells.

Contact between the test substance and the cells that permit measurement of the expression of miR582 is carried out in culture medium. The culture medium is selected as is appropriate in accordance with the cells that permit measurement of the expression of miR582. Examples include minimum essential medium (MEM) containing approximately 5-20% fetal calf serum, Dulbecco's modified Eagle medium (DMEM), and the like. The culture conditions are also decided as is appropriate in the same way. For example, the pH of the medium is approximately 6 to approximately 8, the culture temperature is usually approximately 30 to approximately 40° C., and the culture time is approximately 12 to approximately 72 hours.

The expression level of miR582 can be measured in accordance with the method described in the section "2. Method for predicting the therapeutic effect of a medicine of this embodiment."

The expression levels can preferably be compared based on the existence of a significant difference. Furthermore, the expression level of miR582 in control cells not brought into contact with the test substance may be an expression level measured in advance or an expression level measured simultaneously vis-à-vis measurement of the expression level of miR582 in cells brought into contact with the test substance. However, the expression level measured simultaneously is preferred in view of the accuracy and reproducibility of the experiment.

Substances that upregulate the expression level of miR582 obtained as a result of comparison are selected as substances capable of suppressing the growth of cancer cells and substances capable of inhibiting the metastasis of cancer or the invasive capacity of cancer cells.

Compounds obtained by the screening method of this embodiment are useful as candidates for the development of new cancer therapeutics.

EXAMPLES

Examples of the present invention are explained below. However, the present invention is in no way limited to these examples. Furthermore, in this specification, nucleotide sequences are described from 5' to 3' unless noted otherwise. RNA forming a double strand of SEQ ID NO: 1 and SEQ ID NO: 2 (refer to formula (■)) is abbreviated as "miR582" in the following examples. A double strand formed by SEQ ID NO: 1 and a complementary strand thereof having a base "aa" added to the 3' ends of both strands is abbreviated as "miR582-5p." A double strand formed by SEQ ID NO: 2 and a complementary strand thereof having a base "aa" added to the 3' ends of both strands is abbreviated as "miR582-3p."

Example 1

Expression of miR582 in Bladder Cancer Cells

RNA was purified from the human bladder cancer cell lines UM-UC-3, 5637, T24, and HT1376, the human bladder transitional epithelial papilloma cell line RT4, and the mouse bladder cancer cell line MBT2 cells using QIAzol (product name, Invitrogen) and an miRNeasy Mini Kit (product name, Qiagen) according to the product protocols. Human Bladder Total RNA from Ambion was used for RNA of human bladder cancer cells. The expression of miR582-5p and mirR582-3p was assayed using TaqMan MicroRNA Assays (product name, 7Applied Biosystems). AB17300 (product name, Applied Biosystems) was used in the quantitative PCR reaction, and human RNU6B (4373381, Applied Biosystems) or has-miR-103 (Applied Biosystems) was used as the internal standard. The expression of miR582-5p and miR582-3p was high in human bladder transitional epithelial papilloma cells line RT4 and normal bladder cells. The expression of miR582-5p and miR582-3p was decreased globally in bladder cancer cells UM-UC-3, 5637, HT1376, and MBT2, and expression was clearly decreased in the highly invasive bladder cancer cell lines UM-UC-3, HT1376, and MBT2 (FIG. 1). T24 is a highly invasive bladder cancer cell line, but the expression of miR582-5p and miR582-3p was not significantly decreased in this cell line.

The above results suggested that the expression of miR582-5p and miR582-3p is decreased in a high proportion of bladder cancer cells.

Example 2

Study of the Copy Number of the Chromosomal Region of miR582

Genomic DNA was extracted from human bladder cancer cells UM-UC-3, T24, and HT1376 using a GenElute mammalian genomic DNA mini prep kit (Sigma-Aldrich) according to the product protocol. Quantitative PCR of the miR582 region on chromosome 5812 was conducted using Platinum SYBR Green qPCR SuperMix-UDG (product name, Invitrogen). The primer sequences used in quantitative PCR are shown in SEQ ID NO: 4 and SEQ ID NO: 5.

[Chemical Formula 3]

(SEQ ID NO: 4)
CCACAACAAGTCAATCTGTGC (SEQ ID NO: 5)
TATTGAAGGGGGTTCTGGTG

Assay was conducted by TaqMan Copy Number Reference Assay RNase P(4403326, Applied Biosystems) and Platinum Quantitative PCR SuperMix-UDG (product name, Invitrogen) using RNase P as the internal standard, and the previous quantitative PCR data on the miR582 region were corrected. As a result of assay, the copy number of the chromosomal region of miR582 was decreased to approximately half in UM-UC-3, which are highly metastatic and invasive bladder cancer cells, in comparison to T24 and HT1376 (FIG. 2). The above results suggested the possibility that the copy number of the genome of miR582 is involved in decreased expression of miR582.

Example 3

Growth-Suppressing Activity of miR582 in the Human Bladder Cancer Cell Line UM-UC-3 miR582, miR582-5p, and miR582-3p were used to confirm growth-suppressing activity in the human bladder cancer cell line UM-UC-3. These were all purchased from BONAC. Allstars negative control siRNA (Qiagen) was used as the negative control. Each of the above miRNA was transfected into the UM-UC-3 cell line in a concentration of 25 nM each using DharmaFECT1 (Dharmacon) according to the product protocol. After culturing the cells for 24 hours at 37° C. by 5% $CO_2$, they were re-seeded at 3000 cells/well on 96-well plates. After culturing for three days, the number of surviving cells was evaluated by measuring the 450 nm absorbance by Envision (Perkin Elmer) according to the product protocol using a Tetra Color One Assay Kit (product name, Seikagaku Kogyo).

As a result, cell growth was significantly suppressed in UM-UC-3 cell lines transfected with miR582, miR582-5p, and miR582-3p in comparison to the negative control (FIG. 3, p<0.01). This result clarified that miR582 and the like have activity for suppressing the growth of bladder cancer cells.

Example 4

Invasion-Suppressing Activity of miR582 in the Human Bladder Cancer Cell Line UM-UC-3

The same miR582, miR582-5p, and miR582-3p as were used in Example 3 or Allstars negative control siRNA (Qiagen) were each transfected in a concentration of 25 nM into a UM-UC-3 cell line using DharmaFECT1 (Dharmacon) according to the product protocol. After culturing for 24 hours at 37° C. by 5% $CO_2$, the cells were supplied for cell invasion assay. This assay was conducted using a 24-well Biocoat Matrigel invasion chamber (8 μm, Becton Dickinson) according to the product protocol. Specifically, the cells were sown on the upper chamber of a 24-well plate in a concentration of 100,000 cells/well, and FBS was added in a final concentration of 10% to the culture medium in the lower chamber. After culturing for 24 hours at 37° C. by 5% $CO_2$, the cells attached to the upper chamber side of the permeable membrane were wiped away, and the cells that had invaded the lower chamber side were fixed and stained by Diff-Quick (Sysmex). The number of invading cells in three random fields was counted under a microscope, and the number of invading cells was determined in each experimental group.

As a result, cell invasion was significantly suppressed in UM-UC-3 cells lines transfected with miR582, miR582-5p, and miR582-3p in comparison to the control (FIG. 4, p<0.01). This result clarified that miR582 and the like have activity for suppressing the invasion of bladder cancer cells.

Example 5

Therapeutic Effect of miR582 in a Mouse Bladder Cancer Model

Cancer transplantation was performed by administering 5,000,000 UM-UC-3 cells that express a luciferase gene (UM-UC-3-LUC) into the bladders of mice. Cancer growth and metastasis were observed once a week by in vivo imaging. Specifically, 150 mg/kg of D-luciferrin (Promega) was administered intraperitoneally, and after standing for 10 minutes, the bioluminescence in the cancer tissue was detected by a photon counter using an IVIS Imaging System (Xenogen) according to the product method, and the cancer growth was measured. Data analysis was performed by Living Image software (version 2.5, Xenogen). The size of the cancer transplanted was measured by bioluminescence four days after cancer transplantation, and the mice were divided into two groups so that the luminescence would be equal between groups.

Complexes were formed using the same miR-582 as was used in Example 3 or an miR582-scramble control (SEQ ID NO: 6 and SEQ ID NO: 7) and LIC101 (Nippon Shinyaku) in a 1:16 (w/w) ratio. These complexes were administered transurethrally in a dose of 10 µg (amount of nucleic acid)/70 µL immediately and on days 5, 7, 9, 11, 13, and 15 after cancer transplantation. The bioluminescence was examined 1, 2, 3, and 4 weeks after cancer transplantation, and the size of the cancers was measured.

[Chemical Formula 4]
(SEQ ID NO: 6)
UACGUACGUCGUCUAAUUAAUCU (SEQ ID NO: 7)
AUUAAUUAGACGACGUACGACC As a result, suppression of cancer tissue growth was observed in the miR-582 group from the third week, and significant suppression of cancer growth in comparison to the scramble control was observed in the fourth week (FIG. 5, $p<0.05$). The mice were sacrificed on day 28 after cancer transplantation, and UM-UC-3-LUC that had metastasized to the lungs was detected using the bioluminescence as the indicator. As a result, metastasis was found in five of eight mice in the scramble control group, but metastasis was only found in one of ten mice in the miR582 group (Table 1).

TABLE 1

|  | Metastasis (%) |
| --- | --- |
| Scramble | 5/8 (63) |
| miR-582 | 1/10 (10) |

As a result of assaying the UM-UC-3-LUC that had metastasized to the lungs using the bioluminescence as the indicator, a significant decrease in luminescence was observed in the miR582 group in comparison to the scramble control group (FIG. 6, $p<0.05$).

The above results clarified that miR582 has activity for suppressing the growth and metastasis of bladder cancer cells in an animal model as well.

Example 6

Prediction of the Target Genes of miR582

The following experiments were conducted to identify the target genes of miR582, and candidate target genes were selected in each experiment.

1) Stable expression cells to be used in the following experiments were established as follows. pHA-hAG02-Puro (RA703A-1, SBI) was transfected into L293T cells together with ViraPower Packaging Mix (K4975-00, Invitrogen) according to the product protocol. After culturing the cells for 48 hours at 37° C. by 5% $CO_2$, the culture supernatant was recovered and taken as virus solution. UM-UC-3 cells were infected with the virus according to the product protocol, cultured for two weeks at 37° C. by 5% $CO_2$ in the presence of 2 µg/mL of puromycin, and UM-UC-3/HA-AG02 that stably expresses HA-AG02 was obtained. The pre-miR582 sequence was PCR amplified from genomic DNA of an HT1376 cell line using primers of SEQ ID NO: 8 and SEQ ID NO: 9, and cloned into the ECORI and BamHI sites of a pCDH-CMV-MCS-EF1-GreenPuro cDNA cloning and expression vector (CD513B-1, SBI).

[Chemical Formula 5]
(SEQ ID NO: 8)
AAAGAATTCGTATGTTGCTTCAAGTCATTC (SEQ ID NO: 9)
AAAGGATCCAAAGGCACCATGTAGCTTGTA This plasmid was transfected into L293T cells together with ViraPower Packaging Mix (K4975-00, Invitrogen) according to the product protocol. After culturing the cells for 48 hours at 37° C. by 5% $CO_2$, the culture supernatant was recovered and taken as virus solution. UM-UC-3 cells were infected with the virus according to the product protocol, cultured for two weeks at 37° C. by 5% $CO_2$ in the presence of 2 µg/mL of puromycin, and UM-UC-3/miR582 that stably expresses miR582 was obtained. Lenti-scramble shRNA (MZIPOOOPA-1, SBI) was transfected into L293T cells together with ViraPower Packaging Mix (K4975-00, Invitrogen) according to the product protocol. After culturing the cells for 48 hours at 37° C. by 5% $CO_2$, the culture supernatant was recovered and taken as virus solution. UM-UC-3 cells were infected by the virus according to the product protocol, cultured for two weeks at 37° C. by 5% $CO_2$ in the presence of 2 µg/mL of puromycin, and UM-UC-3/shNC that stably expresses the scramble control shRNA was obtained.

2) miR582 or control siRNA (Allstars negative control siRNA, Qiagen) was transfected into UM-UC-3 cells that express HA-AG02 in a concentration of 25 nM each using DharmaFECT1 (Dharmacon) according to the product protocol, and the cells were cultured for 48 hours at 37° C. by 5% $CO_2$. RNA-binding protein immunoprecipitation (RIP) was then conducted using an RIP-assay kit for microRNA (MBL) and anti-HA agarose beads (Wako Pure Chemicals). The RNA bonded to AG02 was eluted by HA peptide (Wako Pure Chemicals) and extracted and purified using QIAzol (Invitrogen) and an miRNeasy Mini Kit (Qiagen) according to the product protocols. The RNA obtained was labeled by Cy3 using a Low Input Quick Amp Labeling Kit, one color (Agilent) according to the product protocol, hybridized by a SurePrint G3 Human GE microarray kit 8×60 K (product name, Agilent), and microarray data were acquired. The microarray data obtained were analyzed by GeneSpring GX11.5 (Tomy Digital). As a result, 9266 genes were identified as candidate target genes of miR582 that formed complexes with AG02 and miR582.

3) miR582 or Allstars negative control siRNA was transfected into UM-UC-3 cells in a concentration of 25 nM each using DharmaFECT1 (Dharmacon) according to the product protocol. After culturing the cells for 48 hours at 37° C. by 5% $CO_2$, RNA was extracted from each of the cells and purified using QIAzol (Invitrogen) and an miRNeasy Mini Kit (Qiagen) according to the product protocols. The RNA obtained was labeled by Cy3 using a Low Input Quick Amp Labeling Kit, one color (Agilent) according to the product protocol, hybridized by a SurePrint G3 Human GE microarray kit 8×60 K (product name, Agilent), and microarray data were acquired. The microarray data obtained were analyzed by GeneSpring GX11.5 (Tomy Digital). The expression data of the UM-UC-3 cells transfected with miR582 and the UM-UC-3 cells transfected with Allstars siRNA were compared, and 7399 genes the expression of which was decreased in UM-UC-3 cells transfected with miR582 were identified as candidate target genes of miR582.

4) RNA from UM-UC-3/miR582 and UM-UC-3/shNC was extracted and purified using QIAzol (Invitrogen) and an miRNeasy Mini Kit (Qiagen) according to the product protocols. The RNA obtained was labeled by Cy3 using a Low Input Quick Amp Labeling Kit, one color (product name, Agilent) according to the product protocol, hybridized by a SurePrint G3 Human GE microarray kit 8×60 K (product name, Agilent), and microarray data were acquired. The microarray data obtained were analyzed by GeneSpring GX11.5 (Tomy Digital). The expression data of the UM-UC-3 miR582 cells and the UM-UC-3 shNC cells were compared, and 10,203 genes were identified as candidate target genes of miR582 as genes having decreased expression in UM-UC-3 miR582 cells.

5) Two hundred fifty-nine genes (direct candidate target gene group I) that overlapped between the groups of 2), 3), and 4) above were selected as a group of candidate genes that serve as direct targets of miR582. Among them there were 38 genes suggested to have a relationship with cancer in the leterature and the like, and a further 19 genes suggested to have a relationship with the growth, invasion, and metastasis of cancer in the leterature and the like were selected.

6) One thousand five hundred fifty-nine genes (indirect candidate target gene group I) that overlapped between the groups of 3) and 4) above and did not overlap with 2) above were selected as a group of candidate genes that serve as indirect targets of miR582. A further seven genes having an expression variation level of two-fold or greater and a p value of <0.05 in the experiment of 3) above and having an expression variation level of 1.7-fold or greater and a p value of <0.05 in the experiment of 4) were selected.

7) A target scan (http://www.targetscan.org/) was conducted, and a total of 100 genes, 50 having top scores as expected target genes of miR582-5p and 50 having top scores as expected target genes of miR582-3p, were selected. Thirty-five genes were selected as genes suggested to have a relationship to the growth, invasion, and metastasis of cancer in the literature and the like. Twenty genes were selected as genes overlapping with the direct target gene group I of 5) above or the indirect target gene group I of 6).

8) Forty-six genes finally selected by 5), 6), and 7) above were predicted to be target genes of miR582.

Example 7

Identification of Target Genes of miR582

The gene expression of five genes, KCNC1, PGGT1B, LRRK2, DIXDC1, and RAB27A, among the 46 genes predicted to be target genes of mirR582 in Example 6 was studied in UM-UC-3 cells transfected with miR582. The same miR582, miR582-5p, and miR592-3p as were used in Example 3 and control siRNA (Allstars negative control siRNA, Qiagen) were transfected in a concentration of 25 nM each using DharmaFECT1 (Dharmacon) according to the product protocol. The RNA was then extracted and purified from UM-UC-3 cells that had been cultured for 24 hours at 37° C. by 5% $CO_2$ using QIAzol (Invitrogen) and a miRNeasy Mini Kit (Qiagen) according to the product protocols. cDNA was synthesized from the RNA obtained using a High Capacity cDNA Reverse Transcription Kit (product name, Applied Biosystems) according to the product protocol. The cDNA was subjected to quantitative PCR using Platinum SYBR Green qPCR SuperMix-UDG (abovementioned), and each gene was quantified. The expression data of each gene were standardized using β-actin as the internal standard. The primer sequences used in quantitative PCR are shown in SEQ ID NO: 10 and SEQ ID NO: 11 for KCNC1, SEQ ID NO: 12 and SEQ ID NO: 13 for PGGT1B, SEQ ID NO: 14 and SEQ ID NO: 15 for LRRK2, SEQ ID NO: 16 and SEQ ID NO: 17 for RAB27A, SEQ ID NO: 18 and SEQ ID NO: 19 for DIXDC1, and SEQ ID NO: 20 and SEQ ID NO: 21 for β-actin.

[Chemical Formula 6]

```
                               (SEQ ID NO: 10)
ATCTGGGCGCTCTTCGAG (SEQ ID NO: 11)
TCGATCTCCGTCTTGTTCAC (SEQ ID NO: 12)
AGCGCTATTCTTCACTCGAGAC (SEQ ID NO: 13)
CCTGCAGGGAATAAATCCAC (SEQ ID NO: 14)
GGGCTACAACCGGAAAAATAC (SEQ ID NO: 15)
TGATGTCCCAAACGGTCAAG (SEQ ID NO: 16)
AAGAGGAGGAAGCCATAGCAC (SEQ ID NO: 17)
CCATTGGCAGCACTAGTTC (SEQ ID NO: 18)
TACGAAGGGCAACAAAGGTC (SEQ ID NO: 19)
AATGGACTCGCTCTTTGCAC (SEQ ID NO: 20)
GGCACCACCATGTACCCTG (SEQ ID NO: 21)
CACGGAGTACTTGCGCTCAG
```

As a result, the expression of KCNC1, LRRK2, and DIXDC1 was significantly decreased by transfecting miR582, miR582-5p, and miR582-3p into UM-UC-3 cells (FIG. 7, $p<0.01$). The expression of RAB27A was significantly decreased by transfecting miR582 and mirR582-5p into UM-UC-3 cells ($p<0.01$) (FIG. 7). The expression of PGGT1B was significantly decreased by transfecting miR582 into UM-UC-3 cells (FIG. 8, $p<0.01$). Expression also tended to be suppressed by miR582-5p (FIG. 7).

The above results showed that KCNC1, LRRK2, and DIXDC1 are target genes of both the sequences miR582-5p and miR582-3p that construct miR582, but RAB27A is a target gene of the miR582-5p that constructs miR582. They showed that PGGT1B may be a target gene of the miR582-5p that constructs miR582.

Example 8

Analysis of the Mechanism by which miR582 Suppresses Expression of Target Genes

The 3'-UTR region of the KCNC1, PGGT1B, LRRK2, DIXDC1, and RAB27A genes was amplified by PCR from human genomic DNA and cloned to the NotI and XhoI sites of a psiCHECK-2 plasmid (Promega). The PCR primers used in amplification of the 3'-UTR region of KCNC1 (KCNC1-#1; position within KCNC1 mRNA, 3955-5450 bp) are shown in SEQ ID NO: 22 and SEQ ID NO: 23, and the PCR primers used in amplification of the 3'-UTR region of KCNC1(KCNC1-#2; position within KCNC1 mRNA, 5712-6698 bp) are shown in SEQ ID NO: 24 and SEQ ID NO: 25. The PCR primers used in amplification of the 3'-UTR region of PGGT1B (position within PGGT1 mRNA, 1178-2713 bp) are shown in SEQ ID NO: 26 and SEQ ID NO: 27, the PCR primers used in amplification of the 3'-UTR region of LRRK2 (position within LRRK2 mRNA, 7777-9130 bp) are shown in SEQ ID NO: 28 and SEQ ID NO: 29, and the PCR primers used in amplification of the 3'-UTR region of RAB27A (position within RAB27A mRNA, 1988-2533 bp) are shown in SEQ ID NO: 30 and SEQ ID NO: 31. The PCR primers used in amplification of the 3'-UTR region of DIXDC1 (DIXDC1-#1, position within DIXDC1 mRNA, 2908-4420 bp) are shown in SEQ ID NO: 32 and SEQ ID NO: 33, and the PCR primers used in amplification of the 3'-UTR region of DIXDC1 (DIXDC1-#2, position within DIXDC1 mRNA, 5465-5890 bp) are shown in SEQ ID NO: 34 and SEQ ID NO: 35.

[Chemical Formula 7]

```
                                          (SEQ ID NO: 22)
GCTCGAGTAACCCAGAGTTCTTCCCATTCA
                                          (SEQ ID NO: 23)
GCGGCCGCAAAGTCAGCACAGCTGGCTTTT
                                          (SEQ ID NO: 24)
GCTCGAGTAAGCTCTTTTTGACCAGGATGG
                                          (SEQ ID NO: 25)
GCGGCCGCAATCTGGTACATACCGGCAGTT
                                          (SEQ ID NO: 26)
GCTCGAGTAAGGGGGATTTGTAGCATAACTG
                                          (SEQ ID NO: 27)
GCGGCCGCAATACTTTTTCCCCCACCATCA
                                          (SEQ ID NO: 28)
GCTCGAGTAATCACATGGAAAGGGTACTCACA
                                          (SEQ ID NO: 29)
GCGGCCGCAACAATGAAAGAGATAACACTGGAACA
                                          (SEQ ID NO: 30)
GCTCGAGTAAGATGTTCATATTGAAGCAGTCACA
                                          (SEQ ID NO: 31)
GCGGCCGCAATGGGAGTAGTGGAAGGACAG
                                          (SEQ ID NO: 32)
GCTCGAGTAATGAATTGTTGCTTGGATGGA
                                          (SEQ ID NO: 33)
GCGGCCGCAATGTTTGCTGAGAGAAAACTGACA
                                          (SEQ ID NO: 34)
GCTCGAGTAACCACAGGTAATGACCAAGCA
                                          (SEQ ID NO: 35)
GCGGCCGCAATGCAAACCCCATTTTATTCA
```

A quantity of 100 ng of these reporter plasmids and 25 nM each of the same miR582, mirR582-5p, and mirR582-3p as were used in Example 3 or control siRNA (Allstars negative control siRNA, Qiagen) were transfected into UM-UC-3 cells using DharmFECT Duo transfection reagent (Thermo Fisher Scientific) on 96-well plates. After culturing the cells for 24 hours at 37° C. by 5% $CO_2$, dual luciferase assay was conducted using a Dual-Glo Luciferase assay system (Promega) according to the product protocol. The renilla luciferase value was corrected by the firefly luciferase value, and the reporter activity was determined.

As a result, the luciferase activity was significantly decreased by miR582, miR582-5p, and miR582-3p in PGGT1B, LRRK2, and DIXDC1-#1 (FIG. 8, p<0.01). The luciferase activity was significantly decreased by miR582 and miR582-5p in RAB27A (FIG. 8, p<0.01). No decrease in luciferase activity could be found using any miRNA sequence in KCNC1-#1 and KCNC1-#2.

The above results clarified that target sequences of miR582, miR582-5p, and miR582-3p are present in the 3'-UTR of PGGT1B, LRRK2, and DIXDC1. A target sequence of miR582-5p was also clarified to be present in the 3'-UTR of RAB27A. It was also clarified that no target sequence of any one of the miRNA is present in the 3'-UTR of KCNC1, and that the expression of this gene is suppressed indirectly by miR582. A target sequence of miR582-3p was predicted to be present in DIXDC1-#2, but it was clarified that this sequence does not function.

Example 9

Suppression of Protein Expression of Target Genes by miR582 miR582 or control siRNA (Allstars negative control siRNA, Qiagen) was transfected in a concentration of 25 nM each into UM-UC-3 cells using DharmFECT1 (Thermo Fisher Scientific). After culturing for 48 hours at 37° C. by 5% $CO_2$, the cells were recovered and a cell lysate was prepared using M-PER mammalian protein extraction reagent (product name, Pierce). The cell proteins in the lysate were electrophoresed by SDS-PAGE, and Western blotting was carried out by the conventional method. After blocking (Bloking ONE, 03953-95, Nacalai Tesque), anti-KCNC1 antibody (1:500 dilution, ab84823, Abcam), anti-PGGT1B antibody (1:500 dilution, ab55615, Abcam), anti-LRRK2 antibody (1:500 dilution, ab57329, Abcam), anti-DIXDC1 antibody (1:500 dilution, ab67763, Abcam), and anti-RAB27A antibody (1:200 dilution, ab55667, Abcam) were used as primary antibodies. HRP-linked anti-mouse secondary antibody (NA931V, GE Healthcare) was used in a dilution of 1:5000 as the secondary antibody. The target proteins were detected by a Lumino Imager (LAS-3000, Fuji Photo Film) using an ECL Plus Western blotting system (product name, GE Healthcare). As a result, the protein levels of KCNC1, PGGT1B, LRRK2, DIXDC1, and RAB27A were found to be decreased in UM-UC-3 cells transfected with miR582 in comparison to the control (FIG. 9).

The above clarified that miR582 has KCNC1, PGGT1B, LRRK2, DIXDC1, and RAB27A as target genes and has activity for suppressing the expression of their proteins.

Example 10

Knockdown of miR582 Target Genes and Suppressive Effect on Growth of Bladder Cancer Cells The siRNA sequences of KCNC1 used in the following experiment are shown by SEQ ID NO: 36 and SEQ ID NO: 37, the siRNA sequences of PGGT1B are shown by SEQ ID NO: 38 and SEQ ID NO: 39, the siRNA sequences of LRRK2 are shown by SEQ ID NO: 40 and SEQ ID NO: 41, the siRNA sequences of RAB27A are shown by SEQ ID NO: 42 and SEQ ID NO: 43, and the siRNA sequences of DIXDC1 are shown by SEQ ID NO: 44 and SEQ ID NO: 45.

[Chemical Formula 8]

```
                                          (SEQ ID NO: 36)
c c a a c a a g g u a g a g u u c a u T T (SEQ ID NO: 37)
a u g a a c u c u a c c u u g u u g g T T (SEQ ID NO: 38)
g a g a c a a g c a g g u u g a c a a T T (SEQ ID NO: 39)
u u g u c a a c c u g c u u g u c u c T T (SEQ ID NO: 40)
g c a a a u g a a c u a a g a g a u a T T
```

-continued (SEQ ID NO: 41)
uaucucuuaguucauuugcTT (SEQ ID NO: 42)
ggaccagagaguagugaaaTT (SEQ ID NO: 43)
uuucacuacucucugguccTT (SEQ ID NO: 44)
gaacagaacagaagggacaTT (SEQ ID NO: 45)
ugucccuucuguucuguucTT Each siRNA or Allstars negative control siRNA (Qiagen) was transfected in a concentration of 25 nM into UM-UC-3 cells using DharmaFECT1 (Dharmacon) according to the product protocol. After culturing for 24 hours at 37° C. by 5% $CO_2$, the cells were re-seeded on 96-well plates in a concentration of 3000 cells/well. After culturing these cells for another three days, the number of surviving cells was evaluated by measuring the 450 nm absorbance by Envision (Perkin Elmer) according to the product protocol using a Tetra Color One Assay Kit (Seikagaku Kogyo). As a result, cell growth was significantly suppressed in UM-UC-3 cells transfected with all of KCNC1, PGGT1B, LRRK2, DIXDC1, or RAB27A in comparison to the control (FIG. 10, p<0.01). These results clarified that KCNC1, PGGT1B, LRRK2, DIXDC1, and RAB27A, which are target genes of miRR582, have activity to induce the growth of bladder cancer cells.

Example 11

Knockdown of miR582 Target Genes and Suppressive Effect on Invasion of Bladder Cancer Cells siRNA of KCNC1 (SEQ ID NO: 36 and SEQ ID NO: 37), siRNA of PGGT1B (SEQ ID NO: 38 and SEQ ID NO: 39), siRNA of LRRK2 (SEQ ID NO: 40 and SEQ ID NO: 41), siRNA of RAB27A (SEQ ID NO: 42 and SEQ ID NO: 43), siRNA of DIXDC1 (SEQ ID NO: 44 and SEQ ID NO: 45), or Allstars negative control siRNA (Qiagen) was transfected in a concentration of 25 nM into UM-UC-3 cells using DharmaFECT1 (Dharmacon) according to the product protocol. After culturing the cells for 24 hours at 37° C. by 5% $CO_2$, cell invasion assay was performed. This assay was conducted according to the product protocol using a 24-well Biocoat Matrigel invasion chamber (8 Becton Dickinson). Specifically, the cells were seeded on the upper chamber of a 24-well plate in a concentration of 100,000 cells/well, and FBS was added in a final concentration of 10% to the culture medium in the lower chamber. After culturing for 24 hours at 37° C. by 5% $CO_2$, the cells attached to the upper chamber side of the permeable membrane were wiped away, and the cells that had invaded the lower chamber side were fixed and stained by Diff-Quick (Sysmex). The number of invading cells in three random fields was counted under a microscope, and the number of invading cells was determined in each experimental group.

As a result, cell invasion was significantly suppressed in UM-UC-3 cells transfected by KCNC1, PGGT1B, LRRK2, DIXDC1, and RAB27A in comparison to the control (FIG. 11, p<0.01). These results clarified that KCNC1, PGGT1B, LRRK2, DIXDC1, and RAB27A, which are target genes of miR582, have activity to induce invasion of bladder cancer cells.

Example 12

Expression of miR582 in Human Bladder Cancer Specimens

Human bladder tissue was excised from 29 bladder cancer patients by transurethral resection or radical bladder resection and used as specimens. Cancer tissue and normal epithelial tissue were fixed by formalin, embedded in paraffin, made into tissue slices, examined by microscope, and the target cells were obtained by laser capture dissection. RNA from the cells obtained was purified using QIAzol (Invitrogen) and an miRNeasy Mini Kit (Qiagen) according to the product protocols. The expression of miR582-5p and miR582-3p was assayed using miRNA assays (Applied Biosystems). AB17300 (Applied Biosystems) was used in the quantitative PCR reaction, and as-miR-103 (Applied Biosystems) was used as the internal standard. As a result, expression of miR582-5p and miR582-3p was significantly decreased in all cancer cells when the expression of these was compared in noncancer cells and cancer cells from the same patient (graph A in FIG. 12, miR582-5p: p<0.0001, miR582-3p: p=0.0003). In addition, when the number of patients having a 2.5-fold or greater decrease in the expression of miR582-5p or miR582-3p in the cancer cells was grouped by bladder cancer grade, it was judged that the number of patients having decreased expression tended to increase with the cancer grade in all cases (graph B in FIG. 12, Table 2).

TABLE 2

| | Down-regulation in clinical samples (Fold Change > 2.5) | | |
|---|---|---|---|
| | grade1 | grade2 | grade3 |
| miR-582-5p | 33% | 50% | 100% |
| miR-582-3p | 22% | 66.7% | 85.7% |

The above results clarified that the expression of miR582-5p and miR582-3p decreases in human bladder cancer tissue in comparison to normal tissue. It was also clarified that there tends to be a negative correlation between the advance of the cancer and expression of these miRNA.

INDUSTRIAL APPLICABILITY

The medicine for cancer treatment of the present invention is useful in the treatment and prevention of cancer and conditions caused by metastasis of cancer. A method of the present invention can also assess cancer, bladder cancer, or the invasive capacity or metastatic capacity of these cancers, and can provide agents for assessing the therapeutic effect and prognosis of cancer and bladder cancer and screening methods for substances having a suppressive action on the growth of cancer and substances having an inhibitory action on the metastasis of cancer.

The invention claimed is:

1. A method for treating cancer, which comprises administering any of the following (1) to (3) to a mammal:
   (1) a nucleic acid comprising a nucleotide sequence shown by SEQ ID NO: 1 or SEQ ID NO: 2;
   (2) a nucleic acid comprising a nucleotide sequence having 70% or higher sequence identity with SEQ ID NO: 1 or SEQ ID NO: 2 the nucleic acid presenting protein expression-suppressing activity, and
   (3) a single-stranded or double-stranded nucleic acid containing a nucleotide sequence of (1) or (2) above and a sequence complementary to said nucleotide sequence, thereby forming a double-stranded structure in all or part of the strand.

2. The method according to claim 1 wherein said nucleic acid is a double-stranded nucleic acid.

3. The method according to claim 1 wherein said nucleic acid comprises a nucleotide sequence shown by SEQ ID NO: 1 or a partial sequence thereof.

4. The method according to claim 1 wherein said nucleic acid comprises a nucleotide sequence shown by SEQ ID NO: 2 or a partial sequence thereof.

5. The method according to claim 1 wherein said nucleic acid contains a nucleotide sequence of miR582 and presents protein expression-suppressing activity.

6. The method according to claim 1 wherein said nucleic acid is at least one nucleic acid selected from miR582 and precursors thereof.

7. The method according to claim 1 wherein said nucleic acid is miR582.

8. The method according to claim 1 wherein said nucleic acid is a modified nucleic acid.

9. The method according to claim 1 wherein said cancer is a cancer in which the expression of miR582 is decreased.

10. The method according to claim 1 wherein the cancer is bladder cancer.

11. The method according to claim 1 wherein the cancer is bladder cancer of grade 2 or higher.

12. The method according to claim 1 wherein any one of said (1) to (3) is administered transurethrally to a mammal.

13. A method for suppressing or preventing metastasis of cancer, which comprises administering any one of the following (1) to (3) to a mammal:
   (1) a nucleic acid comprising a nucleotide sequence shown by SEQ ID NO: 1 or SEQ ID NO: 2;
   (2) a nucleic acid comprising a nucleotide sequence having 70% or higher sequence identity with SEQ ID NO: 1 or SEQ ID NO: 2 the nucleic acid presenting protein expression-suppressing activity, and
   (3) a single-stranded or double-stranded nucleic acid containing a nucleotide sequence of (1) or (2) above and a sequence complementary to said nucleotide sequence, thereby forming a double-stranded structure in all or part of the strand.

14. The method according to claim 13 wherein any one of said (1) to (3) is administered transurethrally to a mammal.

15. A method for suppressing or preventing metastasis of bladder cancer comprising administering to a mammal in need thereof a medicine comprising a pharmaceutically acceptable carrier and any one of the following (1) to (3) in an aqueous or nonaqueous sterile formulation for parenteral administration:
   (1) a nucleic acid comprising a nucleotide sequence shown by SEQ ID NO: 1 or SEQ ID NO: 2:
   (2) a nucleic acid comprising a nucleotide sequence having 70% or higher sequence identity with SEQ ID NO: 1 or SEQ ID NO: 2 the nucleic acid presenting protein expression-suppressing activity, and
   (3) a single-stranded or double-stranded nucleic acid containing a nucleotide sequence of (1) or (2) above and a sequence complementary to said nucleotide sequence, thereby forming a double-stranded structure in all or part of the strand.

16. The method according to claim 15 wherein any one of said (1) to (3) is administered transurethrally to a mammal.

17. The method according to claim 10 wherein said nucleic acid is a double-stranded nucleic acid.

18. The method according to claim 10 wherein said nucleic acid comprises a nucleotide sequence shown by SEQ ID NO: 1 or a partial sequence thereof.

19. The method according to claim 10 wherein said nucleic acid comprises a nucleotide sequence shown by SEQ ID NO: 2 or a partial sequence thereof.

20. The method according to claim 10 wherein said nucleic acid contains a nucleotide sequence of miR582 and presents protein expression-suppressing activity.

21. The method according to claim 10 wherein said nucleic acid is at least one nucleic acid selected from miR582 and precursors thereof.

22. The method according to claim 10 wherein said nucleic acid is miR582.

23. The method according to claim 10 wherein said nucleic acid is a modified nucleic acid.

24. The method according to claim 10 wherein said cancer is a cancer in which the expression of miR582 is decreased.

25. The method according to claim 10 wherein any one of said (1) to (3) is administered transurethrally to a mammal.

* * * * *